US008877455B2

(12) United States Patent
Parker

(10) Patent No.: US 8,877,455 B2
(45) Date of Patent: Nov. 4, 2014

(54) METHODS FOR CONDUCTING GENETIC ANALYSIS USING PROTEIN POLYMORPHISMS

(76) Inventor: Glendon John Parker, Salt Lake City, UT (US)

(*) Notice: Subject to any disclaimer, the term of this patent is extended or adjusted under 35 U.S.C. 154(b) by 495 days.

(21) Appl. No.: 13/071,249

(22) Filed: Mar. 24, 2011

(65) Prior Publication Data

US 2011/0236918 A1    Sep. 29, 2011

Related U.S. Application Data

(60) Provisional application No. 61/340,918, filed on Mar. 24, 2010.

(51) Int. Cl.
  *C12Q 1/37*        (2006.01)
  *G01N 33/68*      (2006.01)
(52) U.S. Cl.
  CPC ........ *G01N 33/6848* (2013.01); *G01N 2800/60* (2013.01)
  USPC .......................................................... 435/24
(58) Field of Classification Search
  None
  See application file for complete search history.

(56) References Cited

U.S. PATENT DOCUMENTS

| | | | |
|---|---|---|---|
| 6,949,344 B1 * | 9/2005 | Baumgartner ................. | 435/7.1 |
| 2002/0094525 A1 | 7/2002 | McIntosh et al. | |
| 2002/0115074 A1 | 8/2002 | Dattagupta | |
| 2003/0073122 A1 | 4/2003 | Sosnowski et al. | |
| 2003/0113726 A1 | 6/2003 | Tsuchihashi et al. | |
| 2003/0134285 A1 | 7/2003 | Oefner et al. | |
| 2003/0134290 A1 | 7/2003 | Stanton, Jr. et al. | |
| 2003/0180749 A1 | 9/2003 | Koster et al. | |
| 2003/0207297 A1 | 11/2003 | Koster et al. | |
| 2003/0228599 A1 | 12/2003 | Straus | |
| 2004/0229231 A1 | 11/2004 | Frudakis et al. | |
| 2005/0026173 A1 | 2/2005 | Zabeau et al. | |
| 2007/0048735 A1 | 3/2007 | Ecker et al. | |
| 2008/0193922 A1 | 8/2008 | Frudakis | |
| 2008/0203284 A1 | 8/2008 | Grothe, Jr. | |
| 2008/0236249 A1 | 10/2008 | Fernandez de la Mora | |
| 2008/0286783 A1 | 11/2008 | Hosono et al. | |
| 2009/0098551 A1 | 4/2009 | Landers et al. | |
| 2009/0226916 A1 * | 9/2009 | DeSimas et al. .................. | 435/6 |
| 2009/0280095 A1 | 11/2009 | Szabowski et al. | |
| 2009/0307179 A1 | 12/2009 | Colby et al. | |
| 2009/0307180 A1 | 12/2009 | Colby et al. | |
| 2009/0307181 A1 | 12/2009 | Colby et al. | |
| 2009/0317805 A1 | 12/2009 | Wang et al. | |
| 2009/0325303 A1 | 12/2009 | Corino | |
| 2010/0017356 A1 | 1/2010 | Degrave et al. | |
| 2011/0237443 A1 * | 9/2011 | Mulero et al. ..................... | 506/7 |

FOREIGN PATENT DOCUMENTS

| | | |
|---|---|---|
| WO | 0063683 | 10/2000 |
| WO | 2005103069 A1 | 11/2005 |
| WO | 2007134117 A2 | 11/2007 |

OTHER PUBLICATIONS

Ku et al. "Keratine 8 and 18 mutations are risk factors for developing liver disease of multiple etiologies" 2003 Proc. Natal. Acad. Sci. 100(10) 6063-6068.*
Lee et al. "Proteome analysis of human hair shaft" Molecular & Cellular Proteomics 2006 5(5), 789-800.*
Hrdy, Daniel B., et al., Frequency of an Electrophoretic Variant of Hair α Keratin in Human Populations, The American Journal of Human Genetics, v. 29, pp. 98-100, 1977.
Marshall, R.C., et al., Methods and Future Prospects for Forensic Identification of Hairs by Electrophoresis, Journal of the Forensic Science Society, v. 25, pp. 57-66, 1985.
Miyake, B. and Seta, S., Hair Protein Polymorphism and Its Application to Forensic Science Hair Comparison, Forensic Science Review, v. 2, No. 1, pp. 26-36, Jun. 1990.
Wittig, M., Protein Patterns of Keratins—The Probable Role in Forensic Hair Examination, Journal of the Forensic Science Society, v. 22, pp. 387-389, 1982.
Hoehenwarter et al., A rapid approach for phenotype-screening and database Independent detection of cSNP/protein polymorphism using mass accuracy precursor alignment. Proteomics, Oct. 2008, vol. 8, No. 20, pp. 4214-4225.
Ku et al., Keratin 8 and 18 mutations are risk factors for developing liver disease of multiple etiologies. Proceedings of the National Academy of Sciences, May 13, 2003, vol. 100, No. 10, pp. 6063-6068.
Lee et al., Proteome Analysis of Human Hair Shaft: From Protein Identification to Posttranslational Modicication. Molecular & Cellular Proteomics, May 2006, vol. 5, No. 5, pp. 789-800.
Plowman, The proteomics of keratin proteins. Journal of Chromatography B Analytical Technologies in the Biomedical and Life Sciences, Apr. 15, 2007, No. 849, No. 1-2, pp. 181-189.
Plowman et al., Problems Associated with the Identification of Proteins in Homologous Families: The Wool Keratin Family as a Case Study. Analytical Biochemistry, Jan. 15, 2002, vol. 300, No. 2., pp. 221-229.

(Continued)

*Primary Examiner* — Suzanne M Noakes
*Assistant Examiner* — Gerard LaCourciere
(74) *Attorney, Agent, or Firm* — Morriss O'Bryant Compagni, PC

(57) ABSTRACT

Methods and processes for conducting genetic analysis through protein polymorphisms, including identification of individuals, establishment of paternity and measurement of genetic diversity and distance. Some illustrative embodiments of methods of the present invention include the identification of peptide biomarkers using proteomic techniques, including liquid chromatography-tandem mass spectrometry from biological samples, using hair, dentin, or bone as a source of the protein to be analyzed. Other illustrative embodiments include the determination of allelic frequency and feasibility of protein polymorphism peptide biomarkers, and the application of these frequencies to allow statistical analysis and population genetics to be applied to collected biological samples.

22 Claims, 3 Drawing Sheets

(56) References Cited

OTHER PUBLICATIONS

UniProtKB/Swiss-Prot Q14532. Keratin, type I cuticular Ha2. Mar. 2, 2010 [online]. Retrieved from the internet: <URL: http://www.uniprot.org/uniprot/Q14532.txt?version=72> [Retrieved Jun. 17, 2011].

UniProtKB/Swiss-Prot Q99218. Amelogenin, Y isoform. Mar. 2, 2010 [online]. Retrieved from the internet: <URL: http://www.uniprot.org/uniprot/Q99218.txt?version=88> [Retrieved Jun. 17, 2011].

International Search Report and Written Opinion, App. No. PCT/US2011/00550, pp. 1-9, completed Jun. 16, 2011 in Alexandria, Virginia, U.S.

Tsai, T.C., et al., Identification of sex-specific polymorphic sequences in the goat amelogenin gene for embryo sexing, Journal of Animal Science, Mar. 18, 2011, 89, p. 2407-2414.

Lee, Y. J., et al., Proteome Analysis of Human Hair Shaft: From protein identification to posttranslational modification. Molecular & Cell Proteomics, 2006, 5 (5), 789-800.

Yip, Y. L., et al., Annotating Single Amino Acid Polymorphisms in the UniProt/Swiss-Prot Knowledgebase. Human Mutation, 2008, 29 (3), 361-6.

Stapleton, D., et al., Analysis of hepatic glycogen-associated proteins. Proteomics, 2010, 10, 2320-2329.

Cox, J., et al., How much peptide sequence information is contained in ion trap tandem mass spectra? J Am Soc Mass Spectrom 2008, 19 (12), 1813-20.

Backwell, L. et al., Probable human hair found in a fossil *Hyaena* coprolite from Gladysvale cave, South Africa. Journal of Archaeological Science, 2009, 36, 1269-1276.

Gilbert, T. M., et al., Ancient mitochondrial DNA from hair. Current Biology, 2004, 14, (12), R463-4.

Cassiday, L., A new method to extract protein from bone. Journal of Proteome Research, 2007, 6, (6), 2053.

Schweitzer, M. H., et al., Biomolecular Characterization and Protein Sequences of the Campanian Hadrosaur *B. canadensis*. Science AAAS, 2009, vol. 324, 626-31.

Shevchenko, A., et al., Tools for exploring the proteomosphere. Journal of Proteomics, 2009, 72, 137-44.

Wittemyer, G., et al., Where sociality and relatedness diverge: the genetic basis for hierarchical social organization in African elephants. Proceedings of The Royal Society Biological Sciences, 2009, 276, 3513-21.

Blouin, M. S., DNA based methods for pedigree reconstruction and kinship analysis in natural populations. TRENDS in Ecology and Evolution, 2003, 18 (10), 503-511.

Gasbarra, D., et al., Estimating genealogies from linked marker data: a Bayesian approach. BMC Bioinformatics 2007, 8, 411, 1-31.

Wilson, A. S., et al., Yesterday's hair—human hair in archaeology. Biologist, 2001, 48 (5), 213-7.

Jope, E. M., The evolution of plants and animals under domestication: the contribution of studies at the molecular level. Phil. Trans. R. Soc. Lond. B. Biol. Sci., 1976, 275 (936), 99-116.

Jope, E. M., The emergence of man: information from protein systems. Phil. Trans. R. Soc. Lond. B. Biol. Sci., 1981 292 (1057), 121-31.

Kitts, A.; Sherry, S., The Single Nucleotide Polymorphism Database (dbSNP) of Nucleotide Sequence Variation. The NCBI Handbook, Ch. 5, 1-31, 2009.

Barton, S. J.; Whittaker, J. C., Review of factors that influence the abundance of ions produced in a tandem mass spectrometer and statistical methods for discovering these factors. Mass Spectrometry Reviews, 2009, 28 (1), 177-87.

Jobling, M. A., et al., Human Evolutionary Genetics: origins, peoples and disease. Garland Publishing: 2004.

Gstaiger, M.; Aebersold, R., Applying mass spectrometry-based proteomics to genetics, genomics and network biology, Nature Reviews Genetic, 2009 (10), 617-27.

Gysin, R., et al., Skin fibroblast model to study an impaired glutathione Synthesis: Consequences of a genetic polymorphism on the proteome, Brain Research Bulletin, 79 (2009), 46-52.

Marjamaa, A., et al., Common candidate gene variants are associated with QT interval duration in the general population, Journal of Internal Medicine, 2008, 265, 448-458.

Shimizu, A., et al., Detection and Characterization of Variant and Modified Structures of Proteins in Blood and Tissues by Mass Spectrometry, Mass Spectrometry Reviews, 2006, 25, 686-712.

Bunger, M. K., et. al., Detection and Validation of Non-synonymous Coding SNPs from Orthogonal analysis of shotgun Proteomics Data. Journal of Proteome Research, 2007, 6 (6), 2331-40.

Shimomura et al., Polymorphisms in the Human High Sulfur Hair Keratin-associated Protein 1, KAP1, Gene Family, Journal of Biological Chemistry, 2002, 277, 45493-45501.

* cited by examiner

FIGURE 1

| | peptide | | mass | allelic frequency |
|---|---|---|---|---|
| Desmoplakin | | | | |
| I305F | *NTNIAQK* | SEQ ID NO: 125 | 787.418 | 0.78 |
| | NTNFAQK | SEQ ID NO: 126 | 821.403 | 0.22 |
| Y1512C | *VQYDLQK* | SEQ ID NO: 127 | 892.465 | 0.79 |
| | VQCDLQK | SEQ ID NO: 128 | 832.411 | 0.21 |
| Keratin, type II cuticular Hb2 | | | | |
| E219Q | *PCVENEFVALK* | SEQ ID NO: 129 | 1247.622 | 0.99 |
| | PCVQNEFVALK | SEQ ID NO: 130 | 1246.637 | 0.01 |
| E452D | *GAFLYEPCGVSTPVLSTGVLR* | SEQ ID NO: 131 | 2165.119 | 0.04 |
| | GAFLYDPCGVSTPVLSTGVLR | SEQ ID NO: 132 | 2151.103 | 0.68 |
| M458T | GAFLYDPCGVSMPVLSTGVLR | SEQ ID NO: 133 | 2181.096 | 0.27 |
| Keratin, type I cuticular Ha2 | | | | |
| I171T | *MVVNIDNAK* | SEQ ID NO: 74 | 1002.516 | 0.93 |
| | MVVNTDNAK | SEQ ID NO: 75 | 990.48 | 0.05 |
| S222Y | *ADLEAQVESLK* | SEQ ID NO: 134 | 1201.619 | 0.46 |
| | ADLEAQVEYLK | SEQ ID NO: 135 | 1277.65 | 0.54 |
| T339M | *DSLENTLTESEAR* | SEQ ID NO: 58 | 1463.673 | 0.99 |
| | DSLENMLTESEAR | SEQ ID NO: 59 | 1493.666 | 0.01 |
| T395M | *LEGEINTYR* | SEQ ID NO: 3 | 1093.54 | 0.63 |
| | LEGEINMYR | SEQ ID NO: 4 | 1123.533 | 0.37 |
| T427P | *LPCNPCSTPSCTTCVPSPCVTR* | SEQ ID NO: 136 | 2264.972 | 0.19 |
| | LPCNPCSTPSCTTCVPSPCVPR | SEQ ID NO: 137 | 2260.977 | 0.78 |
| R428C | *LPCNPCSTPSCTTCVPSPCVTR* | SEQ ID NO: 136 | 2264.972 | 0.79 |
| | LPCNPCSTPSCTTCVPSPCVTCTVCVPR | SEQ ID NO: 138 | 2867.227 | 0.05 |

FIGURE 2

Keratin, type II cuticular Hb2
KRT82_HUMAN
Q9NSB4
| | | |
|---|---|---|
| E452D | rs1732263 | VAR_032786 |
| M458T | rs2658658 | VAR_032787 |
| E219Q | rs1791634 | VAR_018118 |

Desmoplakin
DESP_HUMAN
P15924
| | | |
|---|---|---|
| I305F | rs17604693. | VAR_033862 |
| Y1512C | rs2076299 | VAR_020468 |
| R1738Q | rs6929069 | VAR_023815 |
| | rs34738426 | VSP_005070 |
| | rs28931610 | VAR_015569 |
| | | VAR_015402 |
| | | VAR_023814 |
| | | VAR_023816 |
| | | VAR_015570 |
| | | VAR_018158 |

Keratin, type I cuticular Ha2
K1H2_HUMAN
Q14532
| | | |
|---|---|---|
| Q72R | rs3744786 | VAR_056011 |
| D151E | rs1111168 | VAR_060237 |
| I171T | rs2071560 | VAR_056012 |
| T573C | rs2071560. | VAR_056013 |
| C726A | rs2071561. | VAR_060238 |
| C1077T | rs16966909 | VAR_056014 |
| C1245T | rs2071563 | VAR_056015 |
| A1266G | rs2604955 | VAR_060239 |
| C1340A | rs2604953 | VAR_060240 |
| C1343T | rs9893787 | VAR_056016 |

Selenium binding protein 1
SBP1_HUMAN
Q13228
| | |
|---|---|
| I122V | rs35396382 |
| F135C | rs1043857 |
| A384T | rs1043860 |
| E367K | rs72710112 |
| A262T | rs11581703 |

Plakophilin-1
PKP1_HUMAN
Q13835
| | | |
|---|---|---|
| 412X432 | | VSP_006735 |
| R116H | rs34626929 | VAR_033526 |
| C161Y | rs34704938 | VAR_033527 |
| I196V | rs35507614 | VAR_033528 |
| G415D | rs1626370 | VAR_053811 |
| A463V | rs1092017 | VAR_062171 |

Junction plakoglobin
PLAK_HUMAN
| | | |
|---|---|---|
| S39SS | | VAR_037803 |
| M697L | rs1126821 | VAR_037804 |

Desmoglein-4
DSG4_HUMAN
Q86SJ6
| | | |
|---|---|---|
| 692alt711 | | VSP_012907 |
| 125X335 | | VAR_021291 |
| A154T | rs13381457 | VAR_048514 |
| I535T | rs7229252 | VAR_033700 |
| I644L | rs4799570 | VAR_024387 |

Stratifin
1433S_HUMAN
P31947
| | | |
|---|---|---|
| 85X116 | | VSP_021768 |
| M155I | rs11542705 | VAR_048095 |

Keratin-associated protein 11-1
KRT11_HUMAN
Q8IUC1
| | | |
|---|---|---|
| C111S | rs9636845 | VAR_053467 |

Keratin, type II cuticular Hb5
KRT85_HUMAN
P78386
| | | |
|---|---|---|
| R78H | rs61630004 | VAR_029657 |
| W155L | rs2852471. | VAR_049804 |

Keratin, type I cytoskeletal 39
K1C39_HUMAN
Q6A163
| | | |
|---|---|---|
| T341M | rs17843021 | VAR_038075 |
| L383M | rs17843023 | VAR_038076 |
| R456Q | rs7213256 | VAR_038077 |

Keratin, type I cuticular Ha5
KRT35_HUMAN
Q92764
| | | |
|---|---|---|
| S36P | rs743686 | VAR_056019 |
| C114Y | rs12451652. | VAR_056020 |
| P443A | rs2071801 | VAR_056021 |

Actin, cytoplasmic 1
ACTB_HUMAN
P60709
| | | |
|---|---|---|
| R183W | | VAR_030026 |
| P243L | rs11546899 | VAR_048185 |

Keratin, type I cuticular Ha4
KRT34_HUMAN
O76011
| | | |
|---|---|---|
| I280T | rs2239710 | VAR_056017 |
| H348R | rs2071599. | VAR_056018 |

Keratin, type II cuticular Hb6
KRT86_HUMAN
O43790
| | | |
|---|---|---|
| N114D | | VAR_018125 |
| N114H | | VAR_023053 |
| E402K | | VAR_018127 |
| E402Q | rs28939669 | VAR_018126 |
| E413D | | VAR_018129 |
| E413K | | VAR_018128 |

Keratin, type II cuticular Hb1
KRT81_HUMAN
Q14533
| | | |
|---|---|---|
| G52R | rs2071588. | VAR_018113 |
| R248L | rs6580873. | VAR_018114 |
| R316C | rs4761786 | VAR_018115 |
| E402K | | VAR_018116 |
| E413K | rs57419521 | VAR_018117 |

Keratin, type II cuticular Hb3
KRT83_HUMAN
P78385
| | | |
|---|---|---|
| R149C | rs2857663 | VAR_018119 |
| I279M | rs2852464 | VAR_018120 |
| E407K | | VAR_023052 |
| H493Y | rs2857671 | VAR_018121 |

Keratin, type I cuticular Ha1
K1H1_HUMAN
Q15323
| | | |
|---|---|---|
| A39G | rs6503628 | VAR_046989 |
| A82V | rs6503627 | VAR_046990 |
| A377V | rs34293483 | VAR_046991 |

Keratin, type I cuticular Ha3-I
KT33A_HUMAN
O76009
| | | |
|---|---|---|
| A270V | rs12937519 | VAR_054432 |

Keratin, type I cuticular Ha3-II
KT33B_HUMAN
Q14525

Protein-glutamine gamma-glutamyltransferase E
TGM3_HUMAN
Q08188
| | | |
|---|---|---|
| T13K | rs214803 | VAR_040067 |
| I163L | rs6604806 | VAR_040068 |
| S249N | rs214814 | VAR_040069 |
| K562R | rs1042617 | VAR_040070 |
| G654A | rs1042617 | VAR_040071 |
| L687M | rs45581032 | VAR_055360 |

Keratin, type II cytoskeletal 1
K2C1_HUMAN
P04264
| | | |
|---|---|---|
| K74I | rs57977969 | VAR_017819 |
| V155D | | VAR_017820 |
| V155G | rs57959072 | VAR_003853 |
| L161P | rs57695159. | VAR_003854 |
| I75X197 | | VAR_038627 |
| S186P | rs60022878 | VAR_003855 |
| N188K | rs59429455 | VAR_017821 |
| N188S | rs58928370 | VAR_003856 |
| N188T | | VAR_017822 |
| S193P | rs60937700 | VAR_003857 |
| L214P | rs61549035. | VAR_017823 |
| I312V | | VAR_003858 |
| I330T | | VAR_003859 |
| D340V | rs58062863. | VAR_017824 |
| Y358N | rs1050872. | VAR_003860 |
| A454S | rs17678945. | VAR_038628 |
| 459X466 | | VAR_038629 |
| I479F | rs61218439. | VAR_017825 |
| I479T | rs57837128. | VAR_017826 |
| Y482C | rs58420087. | VAR_017827 |
| L486P | rs56914602. | VAR_017828 |
| E490Q | rs60279707 | VAR_003861 |
| G537C | | VAR_003862 |
| 560X566 | | VAR_003864 |
| K633R | rs14024 | VAR_003863 |

Fatty acid-binding protein, adipocyte
FABP4_HUMAN
P15090
| | | |
|---|---|---|
| E23D | | VAR_036320 |

Calmodulin-like protein 3
CALL3_HUMAN
P27482

FIGURE 3

```
MGTWILFACLLCAAPAMPLPPHPGHPGYINPSYE................ULTPLKMVSQ.I    45
MGTWILFACLVGAAPAMPLPPHPGHPGYINPSYENSHSQAINVDRIALVLTPLKMYPSMI    60
**********.********.**************.***            **********.* *
RPPYPSYGYEPMGGWLHHQIIPVLSQQHPPTHTLQPHHHIPVVPAQQPVIPQQPHMPVPG   105
RPPYSSYGYEPMGGWLHHQIIPVVSQQHPLTHTLQSHHHIPVVPAQQPRVRQQALMPVPG   120
****.***********.*********.*****  *****.********** **.***  *****
QHSMTPIQHHQPNLPPPAQQPYQPQPVQPQPHQPMQPQPPVHPMQPLPPQPPLPPMPPMQ   165
QQSMTPTQHHQPNLPLPAQQPFQPQPVQPQPHQPMQPQPPVQPMQPLLPQPPLPPMPPLR   180
*.****  ********  ******.**************.***** ***********.:
PLPPHLPDLTLEAWPSTDKTKREEVD  191  AMELX_HUMAN  SEQ ID NO: 139
PLPPILPDLHLEAWPATDKTKQEEVD  206  AMELY_HUMAN  SEQ ID NO: 140
****.****.****.*****.*****
```

METHODS FOR CONDUCTING GENETIC ANALYSIS USING PROTEIN POLYMORPHISMS

CROSS-REFERENCE TO RELATED APPLICATION

This application claims the benefit of U.S. Provisional Application No. 61/340,918, filed Mar. 24, 2010, the disclosure of which is incorporated herein by reference in its entirety.

TECHNICAL FIELD

The invention relates to biotechnology and the fields of genetics and proteomics generally, more particularly to the use of marker polypeptides containing polymorphisms to identify individuals and measure genetic relationships.

BACKGROUND

Genetic analysis has evolved and become a prevalent component in society. It is used to establish paternity, to identify individuals or human remains and conduct anthropological analysis of genetic diversity within populations and genetic distance between populations. It is used to determine susceptibility to hereditary diseases and in treatment protocols for somatic disease, such as cancer.

Molecular genetic analysis however, is almost totally dependent on analysis of deoxyribonucleic acid (DNA). DNA technology has become increasingly sophisticated, sensitive and the threshold for its use has become continually lowered. DNA technology has matured and includes such disparate technology as sequencing technology, polymerase chain reaction (PCR), microarray, and construction and use of DNA libraries. The complete sequence of many genomes has been achieved including human, primates (chimpanzee and orangutan), model organisms (mouse, rat, zebra fish, *drosophila, Caenorhabditis elegans,*) and pathogens. Human genomics has identified genetic structures including genes with, exons, introns, and promoter regions and other coding regions responsible for RNA structures. The genome includes non-coding DNA including long interspersed nuclear elements (LINEs), short interspersed nuclear elements (SINEs), retrovirus-like elements and DNA transposon copies. It also includes chromosomal structures such as centromere and telomere-specific sequences.

DNA also exists in mitochondria. This DNA contains fundamental differences to nuclear DNA, it is circular, has a different genetic code and produces only two RNAs, one in each direction, that contain the code for several genes. These features support the accepted hypothesis that mitochondrial DNA originated from endosymbiotic bacteria. The genetics of mitochondrial DNA are matrilineal.

DNA is the basis of genetic variation, which in turn is the basis for the unique phenotype of each individual. Mutations accumulate over each generation and through recombination, independent assortment and zygote formation result in a unique combination in each individual. The variation occurs within each nucleic structure, ranging in size from single nucleotide polymorphisms (SNPs), element insertion, deletion or expansion to chromosomal duplications, deletions and inversions. As it is inherited, this variation maintains a record of an individual's genetic history.

Technology that detects and records genetic variation can provide information for several purposes. It can determine genetic relationships, such as paternity testing, confirming that an individual is descended from two given individuals. DNA can be used to confirm whether a suspect was at a crime scene. A record of unique genetic markers is also used to provide a measure of genetic diversity within a population and a measure of genetic distance between populations. It is also used to determine if an individual is a carrier for a genetic disease or is predicted to be susceptible to a genetic disease. Matching specific DNA markers with a specific inherited disease phenotype has resulted in the discovery of the specific disease genes and the role of many genes in specific disease pathways and physiological mechanisms.

Extensive efforts have been made to record and annotate the human genome and measure the full extent of genetic variation. This resulted in the human genome project and the dbSNP database (www.ncbi.nlm.nih.gov/SNP/), which records human DNA polymorphisms. Using the National Council of Biotechnology Information SNP database it is now possible to obtain the allelic frequency of each SNP in a population-specific manner.

The use of DNA has distinct limitations. If it is collected from volunteers and isolated and stored appropriately it maintains its quality and can be used indefinitely. For many applications however, DNA collection is not ideal. The backbone of DNA consists of phosphodiester bonds that are vulnerable to hydrolytic attack and oxidation. The nucleobases are susceptible to oxidation, alkylation and condensation reactions. Environmental samples from biological remains, forensic samples or anthropological material contain DNA that has not been kept in ideal conditions and is susceptible to chemical and environmental degradation, reducing the quality and integrity of the resulting data. Many applications of DNA, such as use of forensic material, are limited by the frequent absence of DNA or inability to eliminate environmental contamination.

Accordingly, methods of performing analysis on biological samples that utilized a material other than DNA to allow for the collection and preservation of biological samples in circumstances where DNA may not be present or may be degraded, which enable the investigation, establishment, or exclusion of genetic relationships at a level of precision approaching that of DNA analysis would be an improvement in the art. Such a system allowing for the determination of DNA polymorphisms in a biological sample without DNA analysis would further be an improvement in the art.

SUMMARY

The present invention is directed to methods of conducting genetic analysis through protein polymorphisms, including identification of individuals, establishment of paternity and measurement of genetic diversity and distance. Some illustrative embodiments of methods of the present invention include the identification of peptide biomarkers using proteomic techniques, including liquid chromatography-tandem mass spectrometry from biological samples, using hair, dentin, or bone as a source of the protein to be analyzed. Other illustrative embodiments include the determination of allelic frequency and feasibility of protein polymorphism peptide biomarkers, and the application of these frequencies to allow statistical analysis and population genetics to be applied to collected biological samples.

DESCRIPTION OF THE DRAWING

It will be appreciated by those of ordinary skill in the art that the drawings are for illustrative purposes only. The nature of the present invention, as well as other embodiments of the present invention, may be more clearly understood by reference to the following detailed description of the invention, to the appended claims, and to the drawings.

FIG. 1 is a Table of Candidate Peptide Polymorphic Biomarkers Present in Human Hair. Both reference and polymorphic sequences are present, along with masses and predicted allelic frequencies derived from the HapMap database.

FIG. 2 is a table of the 24 most abundant proteins (name, UNIPROT identifier, primary protein citation number) as detected from the method described in Example 1A. Natural variants occurring in each of these gene products are indicated by amino acid missense or nonsense mutation, reference SNP number (rs#), and SwissProt natural varient identifier (FTId#).

FIG. 3 is an identification of male specific trypsin-digested peptides in the Y-chromosome isoform of amelogenin.

DESCRIPTION OF THE INVENTION

Before the present method is disclosed and/or described, it is to be understood that it is not limited to specific tissues, method of obtaining protein samples or method of protein measurement or detection. It is also to be understood that the terminology used herein is for the purpose of describing particular embodiments and is not intended to be limiting.

As used herein and in the appended claims, the singular forms "a", "an", and "the" include plural reference unless the context clearly dictates otherwise. For example, reference to "a host cell" includes a plurality of such host cells, and reference to the "antibody" is a reference to one or more antibodies and equivalents thereof known to those skilled in the art, and so forth.

As used herein "Peptide," "Polypeptide" and "Protein" include polymers of two or more amino acids of any length, and includes post-translational-modification, without restriction on length unless the context clearly dictates otherwise.

As used herein, "comprising," "including," "containing," "characterized by," and grammatical equivalents thereof are inclusive or open-ended terms that do not exclude additional, unrecited elements or method steps, but also includes the more restrictive terms "consisting of" and "consisting essentially of."

As used herein, "a subject" means a vertebrate, such as a fish (salmon, trout, eel), poultry (chicken), or a mammalian (human, cat, dog, mice, rats, guinea pigs, or other small laboratory animals, or farm animals like ruminants or pigs).

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "suitable" as used herein refers to a group that is compatible with the compounds, products, or compositions as provided herein for the stated purpose. Suitability for the stated purpose may be determined by one of ordinary skill in the art using only routine experimentation.

The term "biomarker" as used herein refers to a biological artifact, particularly protein and/or peptide, that is detectable and contains a polymorphism.

The term "detect" as used herein refers to identification of biomarkers and/or properties and/or parameters of the biomarkers including mass, charge, statistical correlation with reference peptides and probability scores.

The term "tissue" refers to all biological tissue, including human samples, human remains or mummies, or non-human sources, such as zoological and/or preserved remains.

The term "polymorphism" refers to allelic variation in nucleic acid and/or corresponding protein sequences.

As discussed previously herein, the use of DNA for genetic analysis of collected biological samples has distinct limitations. Environmental samples from biological remains, forensic samples or anthropological material contain DNA that has not been kept in ideal conditions and is susceptible to chemical and environmental degradation, reducing the quality and integrity of the resulting data or even the ability to perform analysis. Many applications of DNA, such as use of forensic material, are limited by the frequent absence of DNA in the available biological samples or by the inability to eliminate environmental contamination.

Protein, the translated product of DNA, reflects in an absolute manner the variation present in the coded regions of the genome. Therefore it maintains the genetic variation within the DNA in the form of mutations in the amino acid sequence. It is more abundant than DNA and it has a peptide bond in its backbone resulting in greater chemical stability and longer life in the environment compared to the more fragile DNA. While the earliest credible sequences of DNA are from a 50,000 year old frozen mammoth, proteins have been detected and sequences determined from a 40 million year old hadrosaur.

DNA is often not available in human remains that have been exposed to the environment for prolonged periods. However proteins are present beyond the threshold time point of DNA utility. Human remains have proteins present in hard tissues, such as hair, teeth (dentin) and bone that have the potential to be analyzed for polymorphisms, and as such could be used to identify an individual based on parent or sibling DNA, or identity based on other protein samples from the individual. Samples would be obtained from a range of tissues and a wider range of tissue samples. Identification of protein polymorphisms can help determine the genetic distance from a given genetic population, such as a sub-Saharan population.

While protein cannot be amplified, it can be measured with high precision and great sensitivity using mass spectrometry. Protein samples are digested with trypsin, which cleaves the protein into smaller detectable peptides. The peptides are then resolved using very low flow rate liquid chromatography and are ionized and vaporized using electrospray ionization. The charged peptide is then funneled using electric fields into the mass spectrometer where its mass is measured. It is then fragmented using either collision-induced or electron transfer dissociation and the resulting fragment masses are also measured. Both of these fragmentation methods break the peptide backbone at regular points. This allows the amino acid sequence to be determined. The current technology is sensitive enough to detect attomole levels of material at 1 ppm accuracy.

The process of fragmentation data deconvolution has two basic methods. Information may be interpreted using the data within the sample, based on the intrinsic properties of peptide fragmentation, to provide de novo sequence information. Alternatively, fragmentation data may be compared with predicted sequences derived from genomic databases. This method provides a statistical measure of probability that any fragmentation dataset is the predicted amino acid sequence. This provides accurate interpretation of fragmentation data and is more reliable than de novo sequencing. The accuracy however depends on the presence of the peptide amino acid sequence being in the reference protein database.

The accuracy of amino acid sequencing depends on several factors. The actual sequence needs to be in the reference database. The other factor is the mass accuracy of the mass spectrometer instrument. Ambiguity in the mass data from less accurate instruments results in ambiguity in interpreting the amino acid sequence.

In illustrative methods in accordance with the present invention, biological samples are analyzed by mass spectrometric analysis to obtain peptide sequence data for known proteins in the biological samples. Peptide polymorphisms in the peptide sequence data are then analyzed. In simple situations, the presence or absence of polymorphisms can be used for exclusionary analysis. Where available, the polymorphism data can be compared to known population frequencies using appropriate statistical tools to determine the likelihood of matches and the relative strength of the exclusionary analysis. Suitable biological samples may include hair, bone, dentin, skin or other tissues for which the protein polymorphic data can be assessed.

The following factors need to be considered in identification of peptide polymorphic biomarkers. Suitable biomarkers need to be readily identified in mass spectrometry, as a significant portion of any protein is either not ionized or volatilized resulting in its lack of detection. Preferred polymorphic biomarker peptides should also have a measured informative allelic frequency. Biomarkers should be present in sufficient quantities to be detected in any population. Heterozygosity is also a factor as it may result in non-uniform distribution of polymorphism peptide biomarkers. Several samples therefore should be used to eliminated or confirm the presence of protein polymorphisms, as the utility of allelic frequencies and resulting protein polymorphism biomarkers are a function of degree of sampling taken in the reference population. Since reference databases need to be developed, a lack of adequate sampling could result in inaccurate allelic frequencies leading to inaccurate statistical measurements of identity. Such a shortcoming could be addressed by using multiple markers from a single sample, by use of technique for exclusionary purposes (similar to the rough application of A, AB, B, and O blood types) and ultimately by the continued development of databases containing the requisite frequency data for suitable markers of various proteins in the available samples, as discussed in more detail in the following paragraphs.

In order to be used as a peptide biomarker for a single nucleotide polymorphism ("SNP"), the resulting polymorphic peptides need to be detected. The peptides need to be unique, an issue when investigating the highly homologous family of intermediate filament proteins. Peptides must be unique for a single gene product and nucleotide polymorphism. To be detected peptides need to be within a mass/charge ratio of 400 to 2000. The peptides also need to be volatilized and ionized. Even under ideal conditions coverage of proteins is not 100%, usually being less than 80%. The trypsinized peptides also compete for occupancy for the ion-traps and quadrupoles in the instrument, so detection of given peptides is often contingent on the ionization status of other peptides.

The potential silencing of heterozygotic alleles may also limit the detection of genetic variation. The spatial pattern of gene silencing has the potential to result in non-representative transcription and translation of genetic variation. It also raises the possibility that different hairs from different regions of a single individual may have different expression of polymorphic proteins. Discrimination between homozygotic and hetrozygotic alleles may require more than several hair samples from different regions of the body. Non-detection of another corresponding protein polymorphism cannot be used as evidence of homozygosity. Dependence on allelic frequencies to determine genetic probabilities is not altered by the absence of other allelic variants and therefore provides a more conservative estimate of exclusion or identity.

The dependence on single nucleotide polymorphisms reduces the exclusionary power of the genetic analysis. Only four options are available at any loci, almost always only two options occur. The frequencies of these polymorphisms are generally high and rarely at the ideal frequency of 0.5. More instances of polymorphisms are therefore required to reach equivalent powers of exclusion.

Currently, the determination of amino acid sequence of peptides is dependent on comparison with predicted sequences from reference databases. The dependence on reference databases therefore results in difficulty in detecting the unexpected. The absence of amino polymorphisms in reference databases results in the absence of polymorphic peptides in the analysis. Detection of polymorphic peptides not in the reference database will require the use of custom databases where whole polymorphic protein variants are incorporated. Careful analysis of error-tolerant searches may also provide insight into polymorphisms in an unbiased manner. Environmental and chemical modifications, such as oxidation and hydrolysis also result in changes in peptide mass and difficulty in interpretation of fragmentation data.

The allelic frequencies associated with each nucleotide and amino acid polymorphism are a product of the reference populations used in the single nucleotide polymorphism databases. These can be arbitrary in terms of distribution and sample size. Refinement of allelic frequencies will improve over time as sample sizes of relative populations become sufficient to reduce statistical variation and increase confidence in allelic frequencies for each SNP and respective amino acid polymorphism.

Maximum discriminating power of this analysis will depend on maximum detection of polymorphic peptides, which is a function of maximum detection of unique peptides in any given sample. To maximize accurate yield of peptides two approaches can be taken, physical detection of peptides may increase and reference databases and their use can become more sophisticated. Broadened detection of peptides results from increased resolution using liquid chromatography, increased frequency of data acquisition, more efficient fragmentation and increased mass accuracy that reduces ambiguous data interpretation. These criteria are currently met in the latest generation of ultra high resolution quadrapole-time-of-flight mass spectrometry instruments.

Genetic Analysis Using Variation in Human Hair Protein

Human hair protein is ubiquitous, continually shed, and chemically stable, lasting in the environment long after DNA has degraded. It is very common at crime scenes. Preliminary data shows that hair contains over 300 detectable proteins. The genes of these proteins contain functional Single Nucleotide Polymorphisms (SNPs) that manifest as missense mutations and occur at measurable allelic frequencies. Therefore, any strand of hair has the potential, in its intrinsic amino acid sequences, to provide a statistically conclusive link to any given individual.

In methods in accordance with the present invention, proteins from hair samples are digested with the protease trypsin, cleaving the protein into peptides with molecular weights of roughly 400 to 4000. The resulting complex peptide mixture is then resolved with reversed-phase liquid chromatography, ionized and volatilized, and directed into a mass spectrometer where masses are determined (MS). The instrument then fragments individual peptide backbones and measures the resulting pieces, which have a distinctive pattern ($MS^2$). The information from mass spectrometry, therefore, has three dimensions: time of retention on reversed phase, peptide mass (MS) and individual peptide fragmentation masses ($MS^2$). Mass spectrometry has matured to the point where over 10,000 peptide fragmentations can be obtained per run. The mass accuracy of peptide and fragmentation masses is now 1 ppm in both MS and $MS^2$, removing ambiguity from the analysis.

Proteomic analysis of a hair sample identified 319 proteins at an average of 17.6% coverage. The human genome contains 129,000 non-synonymous or functional single nucleotide polymorphisms (SNPs), 16,766 of which have known allelic frequencies using the Utah and Northern European populations (www.ncbi.nlm.nih.gov/snp/). This is an average of 0.7SNPs per gene which calculates to approximately 230 per the 319 identified proteins. Assuming mass spectrometry coverage of 17.6% we should expect to identify 41 polymorphic peptides per run allowing for meaningful statistical analysis of the resulting discovered polymorphisms. For example, such analysis can be used to confirm or exclude that a hair sample found at a crime scene belongs to a suspect without requiring DNA analysis with a precision comparable to current forensic DNA analysis, to identify human remains when no DNA is available, or to establish genetic relationships such as paternity. Other potential uses include tissue matching to genetically distinctive populations, and providing measures of genetic distance.

Single nucleotide polymorphisms (SNPs) and insertion/deletions (indels) are also highly abundant in the genome. A recent paper focusing on the use of SNPs to generate measures of identity demonstrated that 30 highly polymorphic SNPs were able to generate a combined mean match probability of $4.83 \times 10^{-13}$[1]. Every 5 additional loci would increase the discriminatory power ten-fold. The 1000 genome project records 15,275,256 SNPs and 1,480,877 indels. These are collated in the dbSNP database (www.ncbi.nlm.nih.gov/projects/SNP/) that has a total 30,443,446 *Homo sapiens* SNPs (as of Mar. 18, 2011), 161452 of which are non-synonymous, with 41,928 having an annotated allelic frequency (14,887 when restricted to the Utahn and Northern European population). Assuming that there are 21,000 gene products in the human genome that is an average of roughly 2 genetically informative SNPs per protein. The average protein coverage of the 319 identified proteins from the hair proteome was 17.9%. Therefore the theoretical yield of informative SNPs is roughly 114 (319×2×0.179). SNP variation is not evenly distributed however with the 100 most abundant proteins in the hair proteome having 1294 non-synonymous SNPs with 384 having allelic frequencies (70 when restricted to the Utahn, Northern European CEU database). Preliminary analysis of that data, based on the 18 most abundant proteins, identified 61 polymorphic peptides from 52 SNPs.

Genetic Analysis Using Variation in Human Bone and Teeth Protein

Human bone and teeth are often all that remains in many archeological and forensic contexts. Protein, however, can be preserved in the collagen/hydroxyapatite mineral matrix of these tissues. There are several ways to extract peptide information from such tissues, including a hand-drill, crushing a block of material under liquid nitrogen and demineralization with EDTA or 1.2 M hydrochloric acid. Extracted proteins may be digested with the protease trypsin, cleaving the protein into peptides with molecular weights of roughly 400 to 4000. The resulting complex peptide mixture may then be resolved with reversed-phase liquid chromatography, and analyzed similar to the analysis of hair protein previously discussed herein with the identification of suitable proteins for SNP analysis.

In one example, the sex of sub-adult skeletons cannot be identified where other materials are not present as sexually dimorphic skeletal markers develop during adolescence. This is a major barrier to interpretation and analysis of pre-adult remains in anthropological contexts and can be an impediment to the identification of remains in a forensic context. The development of a consistent, reliable sexing protocol has been described as a "Holy Grail" of osteology and physical anthropology for more than 70 years. Tooth dentine usually provides material for identification of matrilineal mitochondrial DNA haplotype and haplogroup, estimates of nucleotide and gene diversity, and the mean number of pairwise differences but contains no information reflecting biological sex. The Y-chromosome however contains an isoform for amelogenin, which plays a major role in the biogenesis of teeth and has several unique peptides, and has identified male-specific trypsin-digested peptides. (FIG. 3.) By examining the proteomic profiles of teeth and bone tissues, the relative proportions of each isoform of amelogenin may be determined. Once a base line for the relative proportions in samples of known sex is established, tissue from remains of unknown sex may be analyzed to determine the sex thereof.

Example 1A

Identification of an Individual from a Human Hair Sample and Development of Allelic Frequency Comparative Database for Human Hair Proteins Peptide Polymorphisms Human hair consists of an outer cuticle surrounding a shaft consisting primarily of keratin and keratin associated proteins. Hair is made by specialized keratinocytes in the hair follicle. Internal intermediate filaments build up and encase non-keratin proteins before the cell dies, creating a component of the hair shaft that then progresses toward the skin surface. The insoluble component of hair contains over three hundred proteins, a considerable amount of proteomic information.

Hair is significant forensically because it is prevalent at crime scenes and has the potential to physically link an individual to a particular space and time. The evidence is biological and as such, is highly complex. The current methodology however, struggles to fully utilize the information within hair, which up until now has been either morphological or genetic. Each type of information has issues however, morphological analysis is intrinsically subjective and genetic information is limited by the low levels and compromised nature of DNA.

Human hair originates in papilla cells, which reside in the base of the hair follicle in the hair bulbus. These cells produce large amounts of different keratin proteins that displace cellular contents and ultimately result in the cell undergoing apoptosis. This process includes degradation of nuclear DNA. Prior to apoptosis the keratin molecules develop extensive covalent bonds with neighboring keratin molecules, primarily disulphide bonds and transglutamation between glutamtic and lysine residues. This extensive level of covalent bonding is responsible for the chemical toughness and resilience of hair. The transglutamation process is indiscriminate however, many other proteins including metabolic, structural and nuclear proteins, also become covalently attached to, or enmeshed within, the extensive keratin matrix. As described in the literature, there are over 300 proteins detected in the hair shaft, including many proteins that are not normally associated with hair. The keratinization extends beyond the cell through desmosomes and hemidesmosomes. The resulting hair shaft has a variety of anatomical features.

Hair growth can be subdivided into three phases: anagen or growth phase, katagen or transitional phase and the final telogen phase. There are about 100,000 hairs on a (non-bald) human scalp of which 70 to 150 telogen hairs are lost per day. As many hairs again are found on the remainder of the body. Most hairs found at a crime scene are almost always telogen hair shafts that do not have follicular cells and have nuclear DNA levels typically below the level of detection. Several groups have tried to analyze the efficacy of obtaining complete or partial nuclear DNA profiles from hair. The use of mini-STRs, dithiothreitol to break disulphide bonds, and novel DNA extraction techniques has had some success with 60% of samples hair providing partial information on some STR loci. Unfortunately, the DNA is typically found to be highly degraded and yields are particularly vulnerable to chemical treatments such as hair dye or bleaching.

A comparative database of human hair was developed by analyzing the 24 most abundant proteins in human hair for suitable polymorphisms. Using the UNIPROT database that contains a section of natural variation and provides the associated single nucleotide polymorphism (SNP). Accessing the SNP database through the UNIPROT database allows the allelic frequency of each particular polymorphism to be determined relative to the reference sequence. This allowed several pieces of information to be obtained about candidate biomarker polymorphism: the Reference SNP (refSNP) Cluster Report number, the single nucleotide polymorphism, the resulting missense mutation or amino acid polymorphism, the predicted peptide amino acid sequence for both reference and missense trypsin-digested peptides (along with their respective masses), and finally the calculated allelic frequency for the SNP that accounts for the amino acid polymorphism.

The information obtained from the UNIPROT database allowed for a determination as to the presence of nucleotide polymorphisms in the genome of a given individual based purely on the presence of a biomarker peptide in a hair sample, with no application of DNA-based methodology. Furthermore, the determined allelic frequencies of detected biomarker, as recorded in the NCBI SNP database, were used in combination with other polymorphic peptides to calculate the probability that any hair sample comes from the same individual as another hair sample. Likewise, in additional embodiments, a predicted combination of peptide biomarker polymorphisms could be determined using DNA-based methodology, such as SNP microarray chips or polymerase chain reaction, which could then be confirmed using proteomic methodology.

Method for Obtaining Allelic Frequencies of Protein Polymorphisms

Human hair proteins identified from literature, or from the sample obtained from a volunteer, provide a description of proteins present in human hair in order of relative probability. Confirmed members of the hair proteome were submitted to the UNIPROT database, which contains a section on Natural Variation listing all known nucleotide variants in the open reading frame of the gene that result in missense mutations. Each missense mutation is annotated along with the responsible single nucleotide polymorphism, with its single nucleotide polymorphism reference number. These numbers are hyperlinked to the National Council of Biotechnology Institute SNP database, which is a general catalog of genetic polymorphism maintained by the NCBI that is publicly accessible through the URL: www.ncbi.nlm.nih.gov/projects/SNP/. Reference numbers herein are from build release dbSNP build 133, the contents of which are incorporated by reference herein in their entirety.

This database contains, in the geneview section, the annotated nucleotide polymorphism along with the annotated amino acid residue change. The population diversity section of each entry in the database includes information required to derive the allelic frequency of both the nucleotide and amino acid polymorphism. The information comes in several forms, either the frequency of the allelic variant is provided in each reference population or a collated value derived from all populations analyzed. In the case of the former format, the collated value for all populations is determined manually.

As shown in FIG. 1, the UNIPROT and SNP database were used as discussed above to analyze three of these proteins for mis-sense mutations with established allelic frequencies to establish that hair proteins contain evidence of genetic variation. The allelic frequencies of each alternative peptide sequence are depicted in bold and the peptides detected with mass spectrometry are indicated in italics.

Preparation of Protein Samples and Mass Spectrometric Analysis

Hair was treated by washing twice for 2 hours in 50 ml of 10% methanol and once with 100% water. Hair was removed and ground with clean exterior of an Erlenmeyer flask on a glass plate. The powder was collected and treated with 50 mM ammonium bicarbonate containing 1% ProteaseMax and DTT (30 mM). The sample was centrifuged and separated into supernatant and insoluble hair fraction. Trypsin (600 ng) was added to both supernatant and the insoluble hair fraction and incubated at 37° C. temperature overnight. Digested peptide mixture (1 μL of 150 μL) was injected directly on to the ESI Ion-Trap/FTMS hybrid mass spectrometer (LTQ-FT, ThermoElectron, Corp., Waltham, Mass.) without further purification.

An aliquot of 1 μl of the sample was injected onto a nano-LC column (75 μm ID×10 cm, Atlantis C18 RP, 3 μm particle size, Waters, Milford, Mass.) using a nano-LC system (NanoLC 1D, Eksigent Technologies, Dublin, Calif.) with a gradient of 9% to 60% acetonitrile in 0.1% formic acid at 400 mL/min (Supplemental Table 1A) over 120 minutes. Primary mass spectra were acquired in the FTMS portion of the instrument and MS/MS sequence information was collected in the linear ion trap using collision-induced dissociation (CID). Primary mass spectra were acquired with typically better than 2 ppm mass accuracy; CID fragmentation spectra were acquired with less than 0.3 Da mass error.

Data Analysis

Peaklists for database searching were generated for peptide precursor ions (i.e. +1, +2 and/or +3 charge states) and corresponding CID fragmentation data using SEQUEST (BioWorks Browser, revision 3.2, ThermoElectron Corp.) with the default parameters. Resulting DTA files from individual LC/MS/MS runs for each species are concatenated into a single file and analyzed using MASCOT (software version 2.1.03, Matrix Science, Inc., Boston, Mass.). The following MASCOT search parameters were used in the analysis: tryptic-specific peptides, maximum of 3 missed cleavages, no fixed modifications, variable methionine oxidation, mass tolerances of 5 ppm for precursor ions and 0.3 Da for MS/MS CID fragment ions. A significance threshold of p<0.05 for identified proteins was used. Individually identified peptides with expectation scores below 0.05 were considered significant and included. Any protein or peptide with greater than a 5% chance of false assignment were excluded. In order to be classed as a glycogen-associated protein, two unique peptides, with different primary sequence and expectation scores less than 0.05, were required to be identified from the gene product.

The probabilities of identity using allelic frequencies were then determined and polymorphic tryptic peptides were identified. The output from proteomic analysis depends on comparison of peptide and fragmentation masses with those in the reference genomic and proteomic databases. Each match is amenable to statistical analysis, resulting in a probability that the match is incorrect (expectation score <0.05=significant) and a score of likelihood (MOWSE score). Raw mass spectrometric data, usually in an application specific format, is therefore converted to peptide sequences, which in turn are matched to proteins present in the reference databases. The peptides present in the sample can then be matched to those predicted to represent polymorphic variation as described in the above paragraph. The associated frequencies of these polymorphic peptides are depicted in TABLE 1 and can be statistically assessed to provide a probability that a particular hair is associated with a given individuals. One assessment that can be used is Random Match Probability, which is useful as a method of stating the rarity of a genetic profile, as set forth beginning at page 243 of the reference manual *Fundamental of Forensic DNA Typing* by John M. Butler, Elsevier 2010, the contents of which manual are incorporated by reference herein in their entirety.

TABLE 1

Desmoplakin

| R1738Q | SEADSDK SEQ ID NO: 1 | 0.758 |
|---|---|---|
| G5492A | GQSEADSDK SEQ ID NO: 2 | 0.234 | rs6929069

Keratin, type I cuticular Ha2

| T395M | LEGEINTYR SEQ ID NO: 3 | 0.629 |
|---|---|---|
| C1245T | LEGE1NMYR SEQ ID NO: 4 | 0.371 | rs2071563

Plakophilin-1

| R116H | FSSYSQMENWSR SEQ ID NO: 5 | 0.975 |
|---|---|---|
| G598A | HFSSYSQMENWSR SEQ ID NO: 6 | 0.024 | rs34626929

Stratifin

| M155I | SAYQEAMDISK SEQ ID NO: 7 | 0.998 |
|---|---|---|
| G536A | SAYQEAIDISK SEQ ID NO: 8 | 0.003 | rs11542705

Keratin, type I cytoskeletal 39

| L383M | QNQEYEILLDVK SEQ ID NO: 9 | 0.876 |
|---|---|---|
| C1183A | QNQEYEILMDVK SEQ ID NO: 10 | 0.124 | rs17843023

Protein-glutamine gamma-glutamyltransferase

| G843A | SWNGSVEILK SEQ ID NO: 11 | 0.821 |
|---|---|---|
| S249N | NWNGSVEILK SEQ ID NO: 12 | 0.133 | rs214814

Keratin, type II cuticular Hb3

| C900G | DLNMDCIVAEIK SEQ ID NO: 13 | 0.981 |
|---|---|---|
| I279M | DLNMDCMVAEIK SEQ ID NO: 14 | 0.019 | rs2852464

Bleomycin hydrolase

| I443V | HVPEEVLAVLEQEPIILPAWDPMGALA SEQ ID NO: 15 | 0.646 |
|---|---|---|
| A1564G | HVPEEVLAVLEQEPIVLPAWDPMGALA SEQ ID NO: 16 | 0.305 | rs1050565

L-lactate dehydrogenase A chain

| S161R | VIGSGCNLDSAR SEQ ID NO: 17 | 0.276 |
|---|---|---|
| C755G | GCNLDSAR SEQ ID NO: 18 | 0.724 | rs5030621

Example 113

Further Development of an Allelic Frequency Comparative Database for Human Hair Proteins Peptide Polymorphisms A volunteer's hair was washed thoroughly with water and 20% methanol and digested with trypsin in the presence of Protease-Max (Promega Inc.). The resulting peptides were applied to a Thermo-Finnigan Hybrid LC/LTQ/FT MS. The resulting data file was submitted to the MASCOT algorithm using a custom reference database that incorporated some protein polymorphisms. 319 proteins were identified (from 7400 peptides) with an average protein coverage of 20%. The resulting data was searched for polymorphic peptides corresponding to the 40 identified proteins. The results of which are depicted in TABLE II.

In TABLE II, the polymorphic peptides identified in the sample are listed along with the biallellic sequence and the responsible non-synonymous single nucleotide polymorphism (rs#). Allelic frequencies are indicated where known. Each peptide was analyzed for quality of assignment (expectation scores below 0.05 that indicates acceptably low probability of incorrect peptide assignment (p=0.05)), and was submitted to the PROWL database to determine if the sequence could be unambiguously assigned to a single gene. Peptides that were correctly assigned and unambiguous are indicated by allelic frequencies being boxed and in bold. These frequencies may be assessed by Random Match Probability to determine the rarity of a profile. In doing such assessment, it may be advantageous to discard frequencies greater than 0.65 in order to remove the most commonly shared alleles from the analysis to improve the sensitivity of the assessment. Using the data from TABLE II in such an analysis calculates a Random Match Probability of 0.025 or 1 in 40.

TABLE II

| Detected Polymorphic Hair Peptides | | | allelic frequency |
|---|---|---|---|
| Desmoplakin isoform 1 | | | P15924 |
| rs80325569 | NLHSEISGK | SEQ ID NO: 19 | 0.96 |
|  | NLHSEISSK | SEQ IS NO: 20 | 0.04 |
| rs77758574 | TTIHQLTMQK | SEQ ID NO: 21 | 0.94 |
|  | TTIHQLTMQKEEDTSGYR | SEQ ID NO: 22 | 0.94 |
|  | TTIHQLSMQK | SEQ ID NO: 23 | 0.05 |
| rs28763966 | ANSSATETINK | SEQ ID NO: 24 | 0.788 |
|  | ANSSATETIKK | SEQ ID NO: 25 | 0.232 |
| rs28763987 | VQEQELTRLR | SEQ ID NO: 26 | 0.701 |
|  | VQEQELTCLR | SEQ ID NO: 27 | 0.299 |
| rs6929069 | SEADSDKNATILELR | SEQ ID NO: 28 | 0.5 |
|  | LEYDLRRGQSEADSDK | SEQ ID NO: 29 | 0.5 |
| rs116888866 | ISITEGIER | SEQ ID NO: 30 | 0.975 |
|  | ISITEGIEQLIVDSITGQR | SEQ ID NO: 31 | 0.025 |
| Keratin, type II cuticular Hb6 | | | Q43790 |
| rs111429470 | LYEEEIR | SEQ ID NO:32 | 1 |
|  | WLYEEEIR | SEQ ID NO: 33 | 0 |
| rs61914259 | VLQSHISDTVVVK | SEQ ID NO: 34 | N.D. |
|  | ILQSHISDTVVVK | SEQ ID NO: 35 | N.D. |
| Keratin, type II cuticular Hb5 | | | P78386 |
| rs112554450 | EAECVEADSGR | SEQ ID NO: 36 | 0.5 |
|  | EAECVEANSGR | SEQ ID NO: 37 | 0.5 |
| rs61740813 | DVDCAYLR | SEQ ID NO: 38 | 0.959 |
|  | DVDGAYLR | SEQ ID NO: 39 | 0.041 |
| rs117675131 | SSSFSCGSSR | SEQ ID NO: 40 | 0.983 |
|  | QITSGPSAIGGSITVVAPDSCAPCQPLSSSFSCGSSR | SEQ ID NO: 41 | 0.017 |
| Keratin, type II cuticular Hb1 | | | Q14533 |
| rs6580873 | LYEEEIDLQSHISDTSVVVK | SEQ ID NO: 42 | 0.173 |
|  | LYEEEIR | SEQ ID NO: 43 | 0.827 |
|  | ILQSHISDTSYVVK | SEQ ID NO: 44 | 0.827 |
| rs4761786 | HGETLR | SEQ ID NO: 45 | 1 |
|  | HGETLCR | SEQ ID NO: 46 | 0 |
| rs2071588 | GLTGGFGSHSVCGGFR | SEQ ID NO: 47 | 1 |
|  | GLTGGFGSHSVCGR | SEQ ID NO: 48 | 0 |

TABLE II-continued

| Detected Polymorphic Hair Peptides | | allelic frequency |
|---|---|---|
| rs57419521 | LLEGEEQR SEQ ID NO: 49 | N.D. |
| | LLEGK:EQR SEQ ID NO: 50 | N.D. |
| Keratin, type I cuticular Ha3-II | | Q14525 |
| rs12450621 | DNAELENLIR SEQ ID NO: 51 | 0.5 |
| | DNAELK:NLIR SEQ ID NO: 52 | 0.5 |
| rs61441663 | LNVEVDAAPAVDLNQVLNETR SEQ ID NO: 53 | 0.974 |
| | LNVEVDAAPAVDLNR:VLNETR SEQ ID NO: 54 | 0.026 |
| rs79296577 | QVVSSSEQLQSYQAENELR SEQ ID NO: 55 | N.D. |
| | QVVSSSEQLQSYQVENELR SEQ ID NO : 56 | |
| rs114488848 | TVNALEIELQAQHNLR SEQ ID NO: 57 | 0.983 |
| | TLNALEIELQAQHNLR SEQ ID NO: 58 | 0.017 |
| rs71373411 | YSLENTLTESEAR SEQ ID NO: 59 | 0.9 |
| | DSLENTLTESEAR SEQ ID NO: 60 | 0.1 |
| rs34771886 | YSSQLSQVQSLITNVESQLAEIR SEQ ID NO: 61 | 0.5 |
| | YSSQLSQVQSLITNVESQLAEIHSDLER SEQ ID NO: 62 | 0.5 |
| Selenium-binding protein 2 | | Q13228 |
| rs72710112 | GGPVQVLEDEELK SEQ ID NO: 63 | 0.992 |
| | GGPVQVLEDK SEQ ID NO: 64 | 0.008 |
| Keratin, type II cuticular Hb2 | | Q9NSB4 |
| rs61730589 | ELDVDGIIAEIK SEQ ID NO: 65 | 0.986 |
| | ELDVDSIIAEIK SEQ ID NO: 66 | 0.014 |
| rs74942852 | NEILEMNK SEQ ID NO: 67 | 0.989 |
| | K:EILEMNK SEQ ID NO: 68 | 0.011 |
| Bleomycin hydrolase | | |
| I443V | HVPEEVLAVLEQEPIILPAWDPMGALA SEQ ID NO: 15 | 0.646 |
| A1564G | HVPEEVLAVLEQEPIVLPAWDPMGALA SEQ ID NO: 16 | 0.305 |
| Keratin, type I cuticular Ha2 | | Q14532 |
| rs117304287 | ETMQFLNDR SEQ ID NO: 69 | 0.992 |
| | EIMQFLNDR SEQ ID NO: 70 | 0.017 |
| rs1111168 | TIEELQQK SEQ ID NO: 71 | 1 |
| | TIDELQQK SEQ ID NO: 72 | 0 |
| rs1111169 | TIEQLQQK SEQ ID NO: 73 | N.D. |
| rs2071560 | MVVNIDNAK SEQ ID NO: 74 | 0.996 |
| | MVVNTDNAK SEQ ID NO: 75 | 0.004 |
| rs57682233 | TVNTLEIELQAQHSLR SEQ ID NO: 76 | 0.975 |
| | CTVNTLEIELQAQHSLR SEQ ID NO: 77 | 0.025 |
| rs16966929 | DSLENTLTESEAR SEQ ID NO: 78 | 0.996 |
| | DSLENMLTESEAR SEQ ID NO: 79 | 0.004 |
| rs11078993 | YSSQLAQMQCMITNVEAQLAEIR SEQ ID NO: 80 | 0.925 |
| | YSSQLAQMQCMITNVEAQLAEIQADLER SEQ ID NO: 81 | 0.075 |
| rs2604956 | ADLER SEQ ID NO: 82 | 0.9 |
| | AELER SEQ ID NO: 83 | 0.1 |
| | AELERQNQEYQVLLDDVR SEQ ID NO: 84 | 0.1 |
| rs2071563 | LEGEINTYR SEQ ID NO: 3 | 0.492 |
| | ARLEGEINTYR SEQ ID NO: 85 | 0.492 |
| | LEGEINMYR SEQ ID NO: 4 | 0.508 |

TABLE II-continued

| Detected Polymorphic Hair Peptides | | allelic frequency |
|---|---|---|
| rs2604955 | SLLENEDCK SEQ ID NO: 86 | 0.308 |
| | SLLESEDCK SEQ ID NO: 87 | 0.692 |
| 14-3-3 protein sigma | | P31947 |
| rs11542705 | SAYQEAMDISK SEQ ID NO: 88 | 0.998 |
| | SAYQEAIDISK SEQ ID NO: 89 | 0.002 |
| rs77608477 | NLLSVAYK SEQ ID NO: 90 | N.D. |
| | NLLSAAYK SEQ ID NO: 91 | |
| rs78707984 | SAYQEAMDISK SEQ ID NO: 88 | 1 |
| | LAYQEAMDISK SEQ ID NO: 92 | N.D. |
| rs11542705 | SAYQEAIDISK SEQ ID NO: 93 | 0 |
| rs77755255 | EMPPTNPIR SEQ ID NO: 94 | N.D. |
| | EMPPSNPIR SEQ ID NO: 95 | N.D |
| rs75914997 | EMPPTNTIR SEQ ID NO: 96 | N.D |
| Desmoglein-4 | | Q86516 |
| rs76399598 | GEDLERPLELR SEQ ID NO: 97 | 0.992 |
| | GEDLESPLELR SEQ ID NO: 98 | 0.008 |
| rs28380082 | VLDVNDNFPTLEK SEQ ID NO: 99 | N.D |
| | VLDVNDNFPALEK SEQ ID NO: 100 | |
| rs76349777 | NQADFHYSVASQFQMHPTPVR SEQ ID NO: 101 | N.D |
| | QADFHYSVASQFQMNPTPVR SEQ ID NO: 102 | |
| rs35378785 | GSSLLNYVLGTYTAIDLDTGNPATDVR SEQ ID NO: 103 | 0.983 |
| | SSLLNYVLGTYTAIDLDTGNPATDVR SEQ ID NO: 104 | 0.017 |
| rs61734847 | SSTMGTLR SEQ ID NO: 105 | 0.942 |
| | SSTMGALR SEQ ID NO: 106 | 0.058 |
| ATP synthase subunit alpha, mitochondrial | | P25705 |
| rs11541932 | ILGADTSVDLEETGR SEQ ID NO: 107 | 1 |
| | ILGADTSVDIEETGR SEQ ID NO: 108 | 0 |
| rs76002505 | AVDSLVPIGR SEQ ID NO: 109 | 0.903 |
| | AVDSFVPIGR SEQ ID NO: 110 | 0.097 |
| rs77958705/rs | TSIAIDTIINQK SEQ ID NO: 111 | 0.986 |
| | TSIAVDTIINQK SEQ ID NO: 112 | 0.014 |
| rs11541934 | EVAAFAQFGSDLDAATQQILSR SEQ ID NO: 113 | |
| | EVAAFAQ SEQ ID NO: 114 | 0 |
| rs75974428 | QGQYSPMAIEEQVQVIYAGVRGYLDK SEQ ID NO: 115 | 0.847 |
| | QGQYSPMAI SEQ ID NO: 116 | 0.153 |
| Annexin A2 | | P07355 |
| rs75993598 | DALNIETAIK SEQ ID NO: 117 | 0.917 |
| | DALNIK:TAIK SEQ ID NO: 118 | 0.083 |
| rs17845226 | SALSGHLETVILGLLK SEQ ID NO: 119 | 0.865 |
| | SALSGHLETILGLLK SEQ ID NO: 120 | 0.135 |
| rs1059688 | TDLEKDIISDTSGDFRK SEQ ID NO: 121 | N.D. |
| rs41307613 | DIISGTSGDFR SEQ ID NO: 122 | |
| Leucine-rich repeat-containing protein 15 | | Q8TF66 |
| rs13070515 | ELSLGIFGPMPNLR SEQ ID NO: 123 | 0.7 |
| | ELSPGIFGPMPNLR SEQ ID NO: 124 | 0.3 |

The human hair proteins identified from this analysis are added to the comparative database of abundant proteins in human hair with suitable polymorphisms. Accessing the SNP database through the UNIPROT database allows the allelic frequency of each particular polymorphism to be determined relative to the reference sequence. This allowed several pieces of information to be obtained about candidate biomarker polymorphism: the Reference SNP (refSNP) Cluster Report number, the single nucleotide polymorphism, the resulting missense mutation or amino acid polymorphism, the predicted peptide amino acid sequence for both reference and missense trypsin-digested peptides (along with their respective masses), and finally the calculated allelic frequency for the SNP that accounts for the amino acid polymorphism. The inclusion of the additional suitable proteins allows for a higher degree of accuracy when analyzing hair samples.

Example 1C

Development of Additional Database

An initial comparative database of human hair was developed by analyzing the 24 most abundant proteins in human hair for suitable polymorphisms as detected from the method described in Example 1A. Using the UNIPROT database that contains a section of natural variation and provides the associated single nucleotide polymorphism (SNP). Accessing the SNP database through the UNIPROT database allows the allelic frequency of each particular polymorphism to be determined relative to the reference sequence. This allowed several pieces of information to be obtained about candidate biomarker polymorphism: the Reference SNP (refSNP) Cluster Report number, the single nucleotide polymorphism, the resulting missense mutation or amino acid polymorphism, the predicted peptide amino acid sequence for both reference and missense trypsin-digested peptides (along with their respective masses), and finally the calculated allelic frequency for the SNP that accounts for the amino acid polymorphism.

The information obtained from the UNIPROT database allowed for a determination as to the presence of nucleotide polymorphisms in the genome of a given individual based purely on the presence of a biomarker peptide a hair sample, with no application of DNA-based methodology. Furthermore, the determined allelic frequencies of detected biomarker, as recorded in the NCBI SNP database, were used in combination with other polymorphic peptides to calculate the probability that any hair sample comes from the same individual as another hair sample. Likewise, in additional embodiments, a predicted combination of peptide biomarker polymorphisms could be determined using DNA-based methodology, such as SNP microarray chips or polymerase chain reaction, which could then be confirmed using proteomic methodology.

A Table of the 24 most abundant proteins (name, UNIPROT identifier, primary protein citation number) is set forth in FIG. 2. Natural variants occurring in each of these gene products are indicated by amino acid missense or nonsense mutation, reference SNP number (rs#), and SwissProt natural varient identifier (FTId#). This preliminary data may be further built upon, as shown by the results of Example 1B. To further build the database a comprehensive study on a cohort of samples is conducted. Hair and DNA are obtained from 12 unrelated volunteers and two parents and four children. Hair samples are processed as set forth above in Examples 1A or 1B including trypsin cleavage and mass spectral analysis.

The protein identity and peptide coverage in hair samples are confirmed and the polymorphic peptides are identified to create a reference database with all possible missense mutations. The identified polymorphisms are then confirmed using DNA SNP analysis. A custom chip of equivalent responsible SNPs (384 SNPs) is designed once protein polymorphisms are detected and DNA from all human subjects analyzed.

A list of different DNA variants that may be used for identification of individuals using human hair protein follows below. Each is identified by a reference SNP number (rs#) from the NCBI SNP database, build release dbSNP build 133, which is publicly accessible through the URL: www.ncbi.nlm.nih.gov/projects/SNP/ and the contents of which are incorporated by reference herein in their entirety. These have been identified by searching the database for SNPs related to hair proteins that relate to an by amino acid missense or nonsense mutation resulting in a peptide difference that may be detectable in a hair sample using a method in accordance with the principles of the present invention.

rs121918354, rs121913415, rs121913414, rs121913413, rs121913412, rs121913411, rs121913410, rs121913409, rs121913408, rs121913407, rs121913406, rs121913405, rs121913404, rs121913403, rs121913402, rs121913401, rs121913400, rs121913399, rs121913398, rs121913397, rs121913396, rs121913395, rs121913394, rs121913228, rs118203897, rs118203896, rs118203895, rs113994177, rs113994176, rs114998364, rs113905463, rs45581032, rs7272340, rs52800893, rs6048066, rs1126816, rs1126815, rs1042617, rs17313209, rs58885596, rs214830, rs57982162, rs214814, rs60904394, rs52815802, rs3844903, rs214803, rs116974883, rs114174651, rs113688813, rs76914868, rs76252955, rs35987350, rs35967493, rs35805642, rs11544962, rs57010936, rs2305108, rs3852912, rs2230560, rs117814881, rs117748961, rs117510013, rs115454241, rs114001067, rs113413186, rs113320733, rs113255372, rs112942400, rs112743184, rs112548402, rs112376128, rs111954087, rs79554307, rs79011243, rs77958705, rs77926733, rs76399598, rs76349777, rs76002505, rs75974428, rs74896702, rs61734847, rs60800275, rs36040686, rs35547948, rs35378785, rs34620697, rs34413638, rs28380082, rs17856350, rs17856349, rs52806211, rs13381457, rs11874681, rs11541939, rs11541935, rs11541934, rs52814215, rs11541932, rs11541931, rs11541929, rs11541928, rs11541926, rs52813728, rs7229252, rs57544609, rs58134049, rs17716472, rs4799570, rs117891115, rs117610737, rs117304287, rs117138331, rs117083040, rs116901031, rs116384015, rs116221624, rs116216460, rs116116504, rs115962974, rs115806588, rs115778641, rs115680799, rs115534630, rs115505212, rs115137098, rs114643360, rs114488848, rs114467326, rs114453622, rs114438618, rs114422156, rs114395985, rs114289459, rs114125651, rs113931914, rs113879590, rs113833688, rs113792465, rs112895156, rs112831734, rs112806006, rs112787493, rs112570296, rs112553892, rs112544857, rs112475590, rs112444332, rs112308890, rs112065669, rs112018671, rs111993782, rs111918281, rs111861376, rs111531747, rs111344340, rs111342287, rs79955632, rs79843431, rs79458943, rs79320768, rs79296577, rs78437817, rs78297802, rs77919366, rs77906668, rs77779192, rs77688767, rs77277754, rs76423373, rs76416187, rs75952379, rs75790652, rs74605551, rs73983451, rs72830046, rs72471582, rs72074479, rs71672421, rs71373411, rs70964671, rs67537422, rs67537421, rs62642482, rs62642478, rs62642477, rs62066570, rs61747622, rs61741664, rs61741663, rs61741661, rs61741660, rs61740669, rs61740668, rs61740667, rs61738272, rs61735162, rs61460100, rs61434181, rs61157095, rs60712939, rs60118264, rs60035576, rs59878153, rs59616921, rs59510579, rs59317143, rs59296273, rs59175042, rs59075499, rs58901407, rs58852768, rs58735429, rs58597584, rs58414354, rs58149344, rs58120120, rs58075662, rs58026994, rs57989439, rs57909628, rs57784225, rs57758262, rs57682233, rs57536312, rs57019720, rs56809156, rs56707768, rs45557233, rs45546335, rs45507397, rs45489599, rs45444391, rs41283425, rs41283367, rs41283363, rs36019136, rs35710360, rs35291793, rs35285640, rs34771886, rs34548975, rs34528587, rs34293483, rs34151210, rs34137556, rs34019652, rs57516142, rs28940896, rs28674800, rs28411890, rs17855788, rs28470825, rs17855579, rs17850807, rs17848949, rs17848948, rs17848946, rs17848945, rs17848929, rs59902640, rs52800237, rs16966929, rs12947361, rs12947055, rs12946178, rs12937519, rs59654549, rs12451652, rs12450621, rs12051598, rs11657323, rs11552917, rs11552915, rs11550612, rs11547397, rs11547396, rs11547395, rs11547392, rs11547391, rs11547388, rs11546666, rs11275186, rs11268553, rs59123042, rs11078993, rs52836971, rs9904102, rs9903686, rs9903685, rs9893787, rs9890362, rs52822034, rs9675246, rs16966743, rs57751946, rs8082683, rs61020583, rs16966742, rs52822833, rs8069943, rs6503628, rs6503627, rs52807316, rs4595852, rs4363911, rs17857021, rs4261597, rs57183809, rs3744786, rs2604956, rs60774372, rs2604955, rs3809883, rs57617862, rs2604953, rs59835513, rs17581044, rs2301354, rs61572775, rs16966705, rs17859323, rs17846298, rs2239710, rs2229426, rs11550610, rs2229425, rs2229424, rs2229423, rs2229421, rs2228309, rs2228307, rs2228306, rs11550613, rs2228305, rs60687291, rs2071601, rs2071599, rs58844466, rs52800623, rs2071563, rs52794180, rs60448298, rs2071561, rs52810265, rs2071560, rs1140623, rs1140618, rs1140617, rs17845140, rs17857943, rs17848957, rs17400684, rs2228308, rs8069426, rs3204598, rs1140616, rs1140614, rs1140613, rs1140612, rs1140610, rs1140606, rs3192906, rs1132269, rs1132268, rs1132265, rs1132264, rs1132259, rs1132258, rs60597381, rs17858152, rs17857559, rs17844847, rs52834590, rs12937241, rs17415687, rs2230409, rs3182084, rs1126821, rs1111169, rs52829742, rs1111168, rs17495901, rs57843904, rs52830500, rs743686, rs112954819, rs111353136, rs75993598, rs61753428, rs61731567, rs61731034, rs61731031, rs61730842, rs59430203, rs41307613, rs35211583, rs35011360, rs17853396, rs17852168, rs17858041, rs17845226, rs11558375, rs11558370, rs11558365, rs11558360, rs11558358, rs11558354, rs11558352, rs11558351, rs11553794, rs2959910, rs1803909, rs17038531, rs1061241, rs3202288, rs10514, rs117030850, rs113552509, rs111528910, rs111281457, rs45545942, rs45462598, rs61755721, rs45456191, rs45447398, rs17853552, rs17853550, rs11551981, rs11551980, rs11551977, rs11551976, rs11538647, rs52820499, rs10148371, rs17846167, rs17859177, rs1063391, rs3182352, rs1042918, rs3182308, rs1042869, rs11538650, rs1126860, rs3182151, rs17354346, rs17295916, rs11125, rs11001, rs59032052, rs17349557, rs17857427, rs1042188, rs2075600, rs4652, rs61570076, rs2075599, rs3181581, rs17253709, rs17854838, rs4644, rs113780307, rs111398723, rs61736053, rs61945045, rs36216107, rs41290740, rs36215077, rs17076703, rs11554039, rs17076692, rs9511894, rs3764136, rs36216909, rs52836735, rs17790596, rs1803092, rs117820873, rs117675131, rs117108628, rs116444444, rs116003276, rs115379586, rs115355093, rs114920447, rs114447073, rs113612324, rs113592710, rs113341953, rs113026141, rs112554450, rs111866984, rs111540940, rs79897879, rs78482853, rs77846840, rs77331319, rs77154254, rs76972814, rs76579608, rs76412202, rs75818265, rs75808403, rs75723740, rs75711771, rs75007002, rs74942852, rs74773270, rs74660757, rs74407849, rs74095618, rs72351593, rs71791446, rs71764183, rs71445558, rs67486530, rs67486529, rs66529359, rs61917869, rs61740813, rs61740690, rs61730591, rs61730590, rs61730589, rs61730588, rs61730587, rs61731785, rs61630004, rs61622714, rs61616632, rs61549035, rs61485872, rs61226348, rs61218439, rs60937700, rs60765982, rs60537449, rs60526003, rs60447237, rs60359468, rs60297570, rs60279707, rs60022878, rs59612842, rs59431558, rs59429455, rs59208902, rs59169454, rs59151464, rs59089201, rs59044845, rs59022806, rs58949162, rs58928370, rs58773503, rs58453920, rs58422839, rs58420087, rs58381018, rs58373389, rs58193503, rs58062863, rs58008716, rs57977969, rs57959072, rs57837128, rs57802288, rs57728941, rs57695159, rs57650413, rs57510142, rs57419521, rs57149265, rs56914602, rs56850150, rs56829062, rs56821304, rs56033871, rs56003009, rs45541435, rs41291993, rs35699102, rs35460727, rs35460418, rs35353807, rs35124031, rs35043606, rs34787940, rs34187924, rs17678945, rs11550253, rs11550252, rs11550251, rs11550247, rs11550246, rs11550245, rs11549369, rs11549361, rs11549352, rs11549351, rs45486301, rs11549349, rs11549348, rs11549346, rs11549345, rs11549343, rs11549364, rs11549340, rs11549338, rs11549336, rs11549334, rs11549333, rs11549329, rs11549328, rs11549326, rs11549323, rs11549322, rs11549321, rs11549316, rs11547927, rs11547926, rs11547925, rs11547923, rs11547922, rs11542649, rs11542647, rs11542646, rs11542645, rs11542644, rs11542643, rs11170114, rs11064463, rs52791179, rs7966339, rs7315516, rs52831436, rs17433505, rs59358781, rs6580873, rs4761786, rs32.11600, rs59455799, rs2857671, rs59371060, rs59248948, rs17368348, rs56529229, rs3741714, rs2857663, rs2852471, rs2852470, rs17368026, rs57859988, rs2852464, rs2741152, rs52836177, rs17715642, rs57500516, rs3741733, rs2658658, rs61489199, rs2634041, rs2293450, rs2232557, rs2232551, rs2071588, rs1803625, rs1803619, rs1791634, rs52817241, rs1732263, rs1065740, rs1064903, rs1062442, rs3203505, rs1062436, rs3203500, rs1062429, rs3168670, rs1062136, rs52834149, rs3759354, rs1057077, rs59527601, rs1050872, rs3181476, rs1042001, rs60356840, rs56597060, rs52833239, rs17788615, rs3168597, rs710415, rs52792934, rs17677668, rs57390569, rs638043, rs15140, rs17855875, rs52799434, rs3825223, rs3191224, rs1050879, rs14024, rs2230021, rs4134524, rs4986830, rs60823674, rs671, rs116841148, rs113872756, rs113852684, rs113784642, rs113765121, rs113723438, rs113545301, rs79659860, rs79278408, rs77752215, rs76414276, rs75739900, rs73400573, rs71705512, rs61876286, rs34305721, rs11604287, rs11553874, rs11553873, rs11553866, rs11551611, rs11551608, rs11551606, rs11551605, rs11551604, rs11551603, rs11551602, rs11551599, rs11551598, rs5030621, rs3210555, rs77029930, rs75808734, rs11595614, rs11595592, rs11557447, rs11557445, rs11557441, rs2231420, rs118101319, rs115257218, rs114863646, rs114824906, rs79731156, rs77527276, rs77384477, rs76828840, rs76517216, rs62580623, rs61999288, rs61755726, rs61740953, rs56136100, rs35356639, rs13298809, rs11545615, rs11545614, rs11545611, rs11545608, rs11545606, rs11545604, rs11542739, rs11542738, rs52832096, rs9330200, rs4073101, rs9897, rs75629244, rs3204631, rs17413881, rs1051231, rs117775328, rs117441660, rs111879470, rs104894003, rs61747111, rs36081609, rs17851374, rs17850166, rs17850033, rs59308417, rs17849553, rs11547706, rs11546945, rs11546944, rs11546938, rs11546937, rs11546934, rs11546932, rs11546931, rs11546930, rs11546929, rs11546925, rs11546921, rs11546916, rs11546914, rs11546913, rs11546912, rs11546910, rs11546904, rs11546903, rs11546902, rs11546901, rs11546899, rs11546898, rs11546895, rs11546894, rs11538804, rs11538802, rs11538800, rs9769523, rs1059983, rs1133136, rs3178297, rs3194633, rs58254690, rs17350089, rs10256, rs117961973, rs116888866, rs116640800, rs115924520, rs115913473, rs115149625, rs115044490, rs114698706, rs114396009, rs114182342, rs114043911, rs113967308, rs113902911, rs113889645, rs113597419, rs113378925, rs113094932, rs113093944, rs112927420, rs112764594, rs112515836, rs112242645, rs111368396, rs80325569, rs80084141, rs79671583, rs79541520, rs78652302, rs77758574, rs77607116, rs76823038, rs76322151, rs76191712, rs75823494, rs75537269, rs75255708, rs73386641, rs73349469, rs66469215, rs61978632, rs61742483, rs61737311, rs61731476, rs45579941, rs41302885, rs41302883, rs41266815, rs41266813, rs36082484, rs36043209, rs36026202, rs35209214, rs35075242, rs34884895, rs34738426, rs34543842, rs34476546, rs34334797, rs34239595, rs34238014, rs34144478, rs28931610, rs28763971, rs28763967, rs28763966, rs28763965, rs28763961, rs28763958, rs28521706, rs58060459, rs28408581, rs52834913, rs17604693, rs13212226, rs13195710, rs11970638, rs11556692, rs11556658, rs11550843, rs11550840, rs11550818, rs11550816, rs11550811, rs11550792, rs11550789, rs11550267, rs11550259, rs11547330, rs9503469, rs58684673, rs7766641, rs61346221, rs52837086, rs6929069, rs3210532, rs2882585, rs2491080, rs2491079, rs52819261, rs2298090, rs2223591, rs52792530, rs57440467, rs2076299, rs2050949, rs1804839, rs1142845, rs1045614, rs6457453, rs12193267, rs562047, rs3899064, rs483628, rs75873002, rs62641703, rs62623676, rs35655433, rs3175026, rs117047588, rs116413867, rs116058101, rs115716405, rs115653853, rs115555466, rs115366708, rs113411271, rs113243841, rs112573338, rs111979102, rs79479993, rs78861435, rs78426951, rs78142768, rs77750814, rs77624106, rs77064436, rs76189552, rs75495843, rs74795266, rs71811389, rs68115727, rs68115726, rs67701986, rs67701985, rs67701984, rs67701983, rs67701982, rs67701981, rs67701980, rs62240055, rs61755441, rs35523547, rs35288908, rs28931589, rs28931588, rs52793039, rs61442620, rs13070515, rs13060627, rs9837637, rs5848341, rs5848340, rs5848339, rs5848338, rs5848337, rs5848336, rs5848327, rs5848326, rs5848324, rs5848323, rs5848321, rs5848320, rs5848316, rs4135384, rs2364793, rs2364792, rs2364791, rs5848325, rs2364790, rs5848322, rs2364789, rs2364788, rs1131354, rs1050869, rs52803102, rs933135, rs115025658, rs112713797, rs112113500, rs111523825, rs80231183, rs78564312, rs76460220, rs72992288, rs72466451, rs67967266, rs66468541, rs61755731, rs61752176, rs41265953, rs17854949, rs11551350, rs11551347, rs11551345, rs11551342, rs11547647, rs60998476, rs17849710, rs16841870, rs58723229, rs8539, rs116396590, rs113410388, rs112477608, rs112455697, rs111401841, rs80338938, rs79984509, rs79907212, rs79128166, rs78707984, rs78672252, rs78314242, rs77893096, rs77890130, rs77755255, rs77608477, rs76556156, rs76376996, rs76363140, rs75914997, rs74136386, rs72710112, rs71732803, rs71640200, rs71630616, rs66704200, rs66704199, rs62636507, rs62636506, rs62624468, rs61818256, rs61693978, rs61672878, rs61661343, rs61616775, rs61578124, rs61527854, rs61501994, rs61444459, rs61726480, rs61411888, rs61295588, rs61282106, rs61250709, rs61235244, rs61224243, rs61214927, rs61195471, rs61177390, rs61094188, rs61064130, rs61046466, rs60992550, rs60934003, rs60890628, rs60872029, rs60864230, rs60695352, rs60682848, rs60662302, rs60652225, rs60580541, rs60578328, rs60556110, rs60458016, rs60446065, rs60310264, rs60290646, rs60168366, rs60029152, rs59981161, rs59931416, rs59914820, rs59885338, rs59684335, rs59653062, rs59601651, rs59564495, rs59332535, rs59301204, rs59270054, rs59267781, rs59065411, rs59040894, rs59026483, rs58978449, rs58932704, rs58922911, rs58917027, rs58912633, rs58850446, rs58789393, rs58727209, rs58672172, rs58571998, rs58541611, rs58436778, rs58389804, rs58362413, rs58327533, rs58133342, rs58105277, rs58100028, rs58048078, rs58034145, rs58013325, rs57983345, rs57966821, rs57920071, rs57883991, rs57877560, rs57830985, rs57793737, rs57747780, rs57730570, rs57629361, rs57520892, rs57394692, rs57318642, rs57207746, rs57077886, rs57048196, rs57045855, rs56984562, rs56935051, rs56851164, rs56816490, rs56793579, rs56771886, rs56699480, rs56694480, rs56673169, rs56657623, rs41269939, rs61742250, rs41264827, rs36059053, rs35507614, rs35396382, rs34777960, rs34704938, rs34626929, rs34195769, rs61726476, rs28933093, rs59963467, rs28933092, rs57128252, rs28933091, rs61675528, rs28933090, rs60789642, rs28928903, rs58312630, rs28928902, rs58044833, rs28928901, rs60711478, rs28928900, rs17856971, rs17847247, rs12562244, rs11581703, rs58224004, rs11575937, rs11549669, rs11549667, rs11549666, rs11542705, rs11539467, rs10920171, rs3209921, rs2501340, rs58367067, rs1779297, rs58820226, rs52796338, rs1626370, rs1043860, rs1043857, rs1043849, rs61070979, rs13768

Example 2

Identification of Human Remains Using Hair

Human remains are found for which DNA is not available due to the condition of the remains, as from prolonged environmental exposure and the discovery of partial remains. Since DNA is not present, but proteins present in the hard tissue of hair are available, hair samples from such remains are analyzed for polymorphisms. Investigatory samples are prepared and analyzed for polymorphisms as set forth in Examples 1A and 1B. At the same time known reference samples from potential individuals who are suspected to be the source of the remains (such as missing persons from the area where the remains were discovered) are similarly prepared and analyzed. Alternatively, samples from relatives of such persons (such as siblings or parents) are used as reference samples, particularly usings SNPs from DNA samples from the prospective parents. Comparison of suitable peptide polymorphisms in the investigatory samples are compared to those of reference samples to exclude potential identified individuals. For non-excluded individuals, data from comparative databases, such as those developed in accordance with Examples 1A through 1C, may be used to calculate the probability of a positive identification.

Example 2A

Exclusion of Potential Criminal Suspects Using Hair

This technique of Example 2 is used to analyze human hair tissue found at a crime scene against known reference samples taken from known suspects. Comparison of suitable peptide polymorphisms against the reference samples is used to exclude potential suspects. For non-excluded individuals, data from comparative databases, such as those developed in accordance with Examples 1A through 1C, may be used to calculate the probability of a positive identification.

Example 2B

Paternity Exclusion Testing Using Hair

This technique of Example 2 is used to analyze human hair tissue as part of paternity testing. Hair samples from a child for which paternity is to be investigated are prepared and analyzed as set forth in Example 1A or 1B. At the same time known reference samples from potential individuals who are suspected to be the fathers of the child are similarly prepared and analyzed. Comparison of suitable peptide polymorphisms against the reference samples is used to exclude potential fathers. For non-excluded individuals, data from comparative databases, such as those developed in accordance with Examples 1A through 1C, may be used to calculate the probability of a positive identification.

Example 3

Identification of Human Remains Using Skin, Dentin, or Bone

Human remains are found for which DNA is not available due to the condition of the remains, as from prolonged environmental exposure and the discovery of partial remains. Since DNA is not present, but proteins present in hard tissues of skin, dentin, and/or bone are available, a comparative databases of human skin, dentin, and/or bone proteins are developed by analyzing the ten most abundant proteins of each for suitable polymorphisms to use as markers, using the UNI-PROT database that contains a section of natural variation and provides the associated single nucleotide polymorphism (SNP), or other relevant literature or databases as known to those of skill in the art. The allelic frequency of each particular polymorphism is determined relative to the reference sequence, and an approximate allelic frequency for the SNP that accounts for the amino acid polymorphism is calculated.

Samples of skin, dentin, and/or bone from such remains are analyzed for polymorphisms. Investigatory samples are prepared and analyzed for polymorphisms using a protocol similar to those set forth in Examples 1A and 1B. At the same time known reference samples from potential individuals who are suspected to be the source of the remains (such as missing persons from the area where the remains were discovered) are similarly prepared and analyzed. Alternatively, samples from relatives of such persons (such as siblings or parents) are used as reference samples. Comparison of suitable peptide polymorphisms in the investigatory samples are compared to those of the reference samples to exclude potential identified individuals. For non-excluded individuals, data from the comparative database may be used to calculate probabilities of a positive identification.

Example 4

Determination of Relationships for Historic Human Remains

Investigatory hair samples from human remains for a historical group, such as those in archeological or anthropological collections, for which DNA is not available due to the condition of the remains, as from prolonged environmental exposure or otherwise, but for which proteins present in the hard tissue of hair are available, are analyzed for polymorphisms as set forth in Example 2. At the same time known reference samples from present day population groups, or other historical groups, are similarly prepared and analyzed. Comparison of suitable peptide polymorphisms in the investigatory samples are compared to those of the reference samples. Data from comparative databases, such as those developed in accordance with Examples 1A through 1C, may be used to calculate the likely statistics between the groups to examine possible phylogenetic relationships for the study of historical relationships between historic populations and development of modern populations. For example the genetic distance from given genetic populations, such as a sub-Saharan population, can be calculated.

Example 5

Identification of Non-Human Remains Using Hair

Non-human remains are found for which DNA is not available due to the condition of the remains. For example, customs agents find a shipment of products made using the tissues of an endangered species that include hair. Hair samples from such products are analyzed for protein polymorphisms, using a protocol similar to those set forth in Examples 1A and 1B. By comparison of suitable peptide polymorphisms from samples of individual products, it can be determined if the products were prepared from more than one individual of the endangered species. Where reference data is available, as by the development of a comparative database as explained previously herein, data from the comparative database may be used to calculate the source of the remains, as by genetic distance to known population groups for the endangered species.

Example 6

Identification of Non-Human Remains Using Hair

It is often very difficult to obtain usable DNA from a perpetrator in rape kits. This is because the victim's DNA occurs at a much greater percentage than the perpetrators DNA. Some success is achieved through specifically amplifying markers on the male-specific Y-Chromosome. Unfortunately this is patrilineal and has limited genetic power. This sometimes makes it difficult to provide enough probative information to convict. However, genetic polymorphic markers also occur on proteins. Therefore male specific proteins in semen, when detected in a rape kit sample, have the potential to provide genetic information that is autosomal and non-redundant with Y-chromosome specific markers. This will expand the forensically probative information from rape kits.

Male specific proteins from a rape kit sample are analyzed for protein polymorphisms as investigatory samples, using a protocol similar to those set forth in Examples 1A and 1B. At the same time known reference samples from potential individuals who are suspected to be the source of the rape kit sample are similarly prepared and analyzed. Alternatively, samples from relatives of such persons (such as siblings or parents) are used as reference samples. Comparison of suitable peptide polymorphisms in the investigatory samples are compared to those of the reference samples to exclude potential identified individuals. For non-excluded individuals, Random Match probabilities may be calculation using data from a comparative database to calculate probabilities of a positive identification.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein.

The invention claimed is:

1. A method of using protein polymorphism biomarkers to conduct genetic analysis on a proteinaceous tissue sample, the method comprising: extracting a mixture of proteins from the proteinaceous tissue sample; digesting the extracted mixture of proteins with trypsin; identifying a pattern of polymorphic tryptic peptides present within the extracted mixture of proteins; and analyzing the identified polymorphic tryptic peptides present within the extracted mixture of proteins to make a determination as to a genetic relationship of a source of the proteinaceous tissue sample.

2. The method according to claim 1, wherein identifying polymorphic tryptic peptides present within the extracted mixture of proteins comprises using mass spectrometry to determine the peptide residues present in the extracted protein.

3. The method according to claim 2, wherein using mass spectrometry to determine the peptide residues present in the extracted mixture of proteins comprises resolving the digested extracted mixture of proteins with reversed-phase liquid chromatography followed by mass spectrometry to fragment individual peptide backbones within the digested extracted mixture of proteins and then measure the resulting pieces to obtain a distinctive pattern corresponding to the individual peptides present.

4. The method according to claim 1, wherein identifying polymorphic tryptic peptides present within the extracted mixture of proteins comprises identifying polymorphic peptides corresponding to known polymorphic variants of proteins present in the proteinaceous tissue sample that correspond to single nucleotide polymorphisms.

5. The method according to claim 4, wherein identifying polymorphic peptides corresponding to known polymorphic variants of proteins present in the proteinaceous tissue that correspond to single nucleotide protein polymorphisms comprises identifying polymorphic peptides corresponding to single nucleotide protein polymorphic variants selected from the group consisting of at least one of desmoplakin; keratin, type I cuticular HA2; plakophilin-1; stratifin; keratin, type I cytoskeletal 39; protein-glutamine gamma-glutamyltransferase; keratin, type II cuticular Hb1; keratin, type II cuticular Hb3; keratin, type II cuticular Hb5; keratin, type II cuticular Hb6; bleomycin hydrolase; L-lactate dehydrogenase A chain; keratin, type I cuticular Ha2; keratin, type I cuticular Ha3-II; selenium-binding protein 1; 14-3-3 protein sigma; desmoglein-4; ATP synthase subunit alpha, mitochondrial; annexin A2; and leucine-rich repeat-containing protein 15.

6. The method according to claim 4, wherein identifying polymorphic peptides corresponding to known polymorphic variants of proteins present in the proteinaceous tissue sample that correspond to single nucleotide polymorphisms comprises identifying polymorphic peptides correspond known single nucleotide polymorphisms that are missense mutations.

7. The method of claim 4, wherein analyzing the identified polymorphic tryptic peptides present within the extracted mixture of proteins to make a determinations as to a genetic relationship of a source of the proteinaceous tissue sample comprises comparing the presence of the individual protein polymorphism biomarkers identified from the polymorphic tryptic peptides to reference protein polymorphism biomarkers in a database to conduct genetic analysis.

8. The method of claim 7, wherein the genetic analysis comprises calculation of a probability that the proteinaceous tissue sample originated with a particular individual, or calculation of a genetic distance between the tissue sample and a known genetic population.

9. The method of claim 7, wherein the genetic analysis comprises exclusion of potential individuals, identification of a specific individual, or an identification of paternity.

10. The method of claim 7, wherein the genetic analysis comprises calculation of a Random Match Probability.

11. The method according to claim 1, wherein identifying polymorphic tryptic peptides present within the extracted mixture of proteins comprises identifying polymorphic peptides corresponding to male specific trypsin-digested peptides in the Y-chromosome isoform of amelogenin.

12. The method of claim 1, wherein the proteinaceous tissue sample comprises human hair, bone or tooth tissue.

13. A process for conducting genetic analysis on a hair sample, comprising: extracting a mixture of proteins from the hair sample; digesting the extracted proteins with trypsin; identifying a pattern of tryptic peptides present within the extracted mixture of proteins; and analyzing the identified pattern of tryptic peptides present within the extracted mixture of proteins to identify protein polymorphisms of interest to make a determination as to a genetic relationship of a source of the hair sample.

14. The process according to claim 13, wherein identifying tryptic peptides present within the extracted mixture of proteins comprises using mass spectrometry to determine the peptide residues present in the extracted protein.

15. The process according to claim 14, wherein using mass spectrometry to determine the peptide residues present in the extracted mixture of proteins comprises resolving digested extracted protein with reversed-phase liquid chromatography followed by mass spectrometry to fragment individual peptide backbones within the digested extracted mixture of proteins and then measuring the resulting pieces to obtain a distinctive pattern corresponding to the individual peptides present.

16. The process according to claim 13, wherein analyzing the identified pattern of tryptic peptides present within the extracted mixture of proteins to identify protein polymorphisms of interest to make a determination as to a genetic relationship of a source of the hair sample comprises identifying polymorphic peptides corresponding to known polymorphic variants of proteins present in hair tissue that correspond to single nucleotide protein polymorphisms.

17. The process according to claim 16, wherein identifying polymorphic peptides corresponding to known polymorphic variants of proteins present in hair tissue that correspond to single nucleotide protein polymorphisms comprises identifying polymorphic peptides corresponding to single nucleotide protein polymorphic variants selected from the group consisting of at least one of desmoplakin; keratin, type I cuticular Ha2; plakophilin-1; stratifin; keratin, type I cytoskeletal 39; protein-glutamine gamma glutamyltransferase; keratin, type II cuticular keratin, type II cuticular Hb3; keratin, type II cuticular Hb5; keratin, type II cuticular Hb6; bleomycin hydrolase; L-lactate dehydrogenase A chain; keratin, type I cuticular Ha2; keratin, type I cuticular Ha3-II; selenium-binding protein 1; 14-3-3 protein sigma; desmoglein-4; ATP synthase subunit alpha, mitochondrial; annexin A2; and leucine-rich repeat containing protein 15.

18. The process according to claim 16, wherein analyzing the identified pattern of tryptic peptides present within the extracted mixture of proteins to identify protein polymorphisms of interest to make a determination as to a genetic relationship of a source of the hair sample further comprises comparing the presence of identified single nucleotide protein polymorphisms within the hair sample to reference protein polymorphism biomarkers in a database to conduct genetic analysis.

19. The process of claim 18, wherein making a determination as to a genetic relationship of a source of the hair sample further comprises calculation of a probability that the hair sample originated with a particular individual, or calculation of a genetic distance between the source of the hair sample and a known genetic population.

20. The process of claim 18, wherein making a determination as to a genetic relationship of a source of the hair sample comprises exclusion of potential individuals, identification of a specific individual, or an identification of paternity.

21. The process of claim 18, wherein the making a determination as to a genetic relationship of a source of the hair sample comprises calculation of a Random Match Probability.

22. The process according to claim 13, wherein digesting the extracted mixture of proteins with trypsin comprises digesting the extracted mixture of proteins with trypsin in the presence of another protease.

* * * * *

SEQUENCE LISTING

```
<160> NUMBER OF SEQ ID NOS: 140

<210> SEQ ID NO 1
<211> LENGTH: 7
<212> TYPE: PRT
<213> ORGANISM: Homo sapiens

<400> SEQUENCE: 1

Ser Glu Ala Asp Ser Asp Lys
1               5

<210> SEQ ID NO 2
<211> LENGTH: 9
<212> TYPE: PRT
<213> ORGANISM: Homo sapiens

<400> SEQUENCE: 2

Gly Gln Ser Glu Ala Asp Ser Asp Lys
1               5

<210> SEQ ID NO 3
<211> LENGTH: 9
<212> TYPE: PRT
<213> ORGANISM: Homo sapiens

<400> SEQUENCE: 3

Leu Glu Gly Glu Ile Asn Thr Tyr Arg
1               5

<210> SEQ ID NO 4
<211> LENGTH: 9
<212> TYPE: PRT
<213> ORGANISM: Homo sapiens

<400> SEQUENCE: 4

Leu Glu Gly Glu Ile Asn Met Tyr Arg
1               5

<210> SEQ ID NO 5
<211> LENGTH: 12
<212> TYPE: PRT
<213> ORGANISM: Homo sapiens

<400> SEQUENCE: 5

Phe Ser Ser Tyr Ser Gln Met Glu Asn Trp Ser Arg
1               5                   10

<210> SEQ ID NO 6
<211> LENGTH: 13
<212> TYPE: PRT
<213> ORGANISM: Homo sapiens
```

<400> SEQUENCE: 6

His Phe Ser Ser Tyr Ser Gln Met Glu Asn Trp Ser Arg
1               5                   10

<210> SEQ ID NO 7
<211> LENGTH: 11
<212> TYPE: PRT
<213> ORGANISM: Homo sapiens

<400> SEQUENCE: 7

Ser Ala Tyr Gln Glu Ala Met Asp Ile Ser Lys
1               5                   10

<210> SEQ ID NO 8
<211> LENGTH: 11
<212> TYPE: PRT
<213> ORGANISM: Homo sapiens

<400> SEQUENCE: 8

Ser Ala Tyr Gln Glu Ala Ile Asp Ile Ser Lys
1               5                   10

<210> SEQ ID NO 9
<211> LENGTH: 12
<212> TYPE: PRT
<213> ORGANISM: Homo sapiens

<400> SEQUENCE: 9

Gln Asn Gln Glu Tyr Glu Ile Leu Leu Asp Val Lys
1               5                   10

<210> SEQ ID NO 10
<211> LENGTH: 12
<212> TYPE: PRT
<213> ORGANISM: Homo sapiens

<400> SEQUENCE: 10

Gln Asn Gln Glu Tyr Glu Ile Leu Met Asp Val Lys
1               5                   10

<210> SEQ ID NO 11
<211> LENGTH: 10
<212> TYPE: PRT
<213> ORGANISM: Homo sapiens

<400> SEQUENCE: 11

Ser Trp Asn Gly Ser Val Glu Ile Leu Lys
1               5                   10

<210> SEQ ID NO 12
<211> LENGTH: 10
<212> TYPE: PRT
<213> ORGANISM: Homo sapiens

<400> SEQUENCE: 12

Asn Trp Asn Gly Ser Val Glu Ile Leu Lys
1               5                   10

<210> SEQ ID NO 13
<211> LENGTH: 12
<212> TYPE: PRT
<213> ORGANISM: Homo sapiens

<400> SEQUENCE: 13

Asp Leu Asn Met Asp Cys Ile Val Ala Glu Ile Lys
1               5                   10

<210> SEQ ID NO 14
<211> LENGTH: 12
<212> TYPE: PRT
<213> ORGANISM: Homo sapiens

<400> SEQUENCE: 14

Asp Leu Asn Met Asp Cys Met Val Ala Glu Ile Lys
1               5                   10

<210> SEQ ID NO 15
<211> LENGTH: 27
<212> TYPE: PRT
<213> ORGANISM: Homo sapiens

<400> SEQUENCE: 15

His Val Pro Glu Glu Val Leu Ala Val Leu Glu Gln Glu Pro Ile Ile
1               5                   10                  15

Leu Pro Ala Trp Asp Pro Met Gly Ala Leu Ala
            20                  25

<210> SEQ ID NO 16
<211> LENGTH: 27
<212> TYPE: PRT
<213> ORGANISM: Homo sapiens

<400> SEQUENCE: 16

His Val Pro Glu Glu Val Leu Ala Val Leu Glu Gln Glu Pro Ile Val
1               5                   10                  15

Leu Pro Ala Trp Asp Pro Met Gly Ala Leu Ala
            20                  25

<210> SEQ ID NO 17
<211> LENGTH: 12
<212> TYPE: PRT
<213> ORGANISM: Homo sapiens

<400> SEQUENCE: 17

Val Ile Gly Ser Gly Cys Asn Leu Asp Ser Ala Arg
1               5                   10

<210> SEQ ID NO 18
<211> LENGTH: 8
<212> TYPE: PRT
<213> ORGANISM: Homo sapiens

<400> SEQUENCE: 18

Gly Cys Asn Leu Asp Ser Ala Arg
1               5

<210> SEQ ID NO 19
<211> LENGTH: 9
<212> TYPE: PRT
<213> ORGANISM: Homo sapiens

<400> SEQUENCE: 19

Asn Leu His Ser Glu Ile Ser Gly Lys
1               5

```
<210> SEQ ID NO 20
<211> LENGTH: 9
<212> TYPE: PRT
<213> ORGANISM: Homo sapiens

<400> SEQUENCE: 20

Asn Leu His Ser Glu Ile Ser Ser Lys
1               5

<210> SEQ ID NO 21
<211> LENGTH: 10
<212> TYPE: PRT
<213> ORGANISM: Homo sapiens

<400> SEQUENCE: 21

Thr Thr Ile His Gln Leu Thr Met Gln Lys
1               5                   10

<210> SEQ ID NO 22
<211> LENGTH: 18
<212> TYPE: PRT
<213> ORGANISM: Homo sapiens

<400> SEQUENCE: 22

Thr Thr Ile His Gln Leu Thr Met Gln Lys Glu Glu Asp Thr Ser Gly
1               5                   10                  15

Tyr Arg

<210> SEQ ID NO 23
<211> LENGTH: 10
<212> TYPE: PRT
<213> ORGANISM: Homo sapiens

<400> SEQUENCE: 23

Thr Thr Ile His Gln Leu Ser Met Gln Lys
1               5                   10

<210> SEQ ID NO 24
<211> LENGTH: 11
<212> TYPE: PRT
<213> ORGANISM: Homo sapiens

<400> SEQUENCE: 24

Ala Asn Ser Ser Ala Thr Glu Thr Ile Asn Lys
1               5                   10

<210> SEQ ID NO 25
<211> LENGTH: 11
<212> TYPE: PRT
<213> ORGANISM: Homo sapiens

<400> SEQUENCE: 25

Ala Asn Ser Ser Ala Thr Glu Thr Ile Lys Lys
1               5                   10

<210> SEQ ID NO 26
<211> LENGTH: 10
<212> TYPE: PRT
<213> ORGANISM: Homo sapiens

<400> SEQUENCE: 26

Val Gln Glu Gln Glu Leu Thr Arg Leu Arg
1               5                   10
```

```
<210> SEQ ID NO 27
<211> LENGTH: 10
<212> TYPE: PRT
<213> ORGANISM: Homo sapiens

<400> SEQUENCE: 27

Val Gln Glu Gln Glu Leu Thr Cys Leu Arg
1               5                   10

<210> SEQ ID NO 28
<211> LENGTH: 15
<212> TYPE: PRT
<213> ORGANISM: Homo sapiens

<400> SEQUENCE: 28

Ser Glu Ala Asp Ser Asp Lys Asn Ala Thr Ile Leu Glu Leu Arg
1               5                   10                  15

<210> SEQ ID NO 29
<211> LENGTH: 16
<212> TYPE: PRT
<213> ORGANISM: Homo sapiens

<400> SEQUENCE: 29

Leu Glu Tyr Asp Leu Arg Arg Gly Gln Ser Glu Ala Asp Ser Asp Lys
1               5                   10                  15

<210> SEQ ID NO 30
<211> LENGTH: 9
<212> TYPE: PRT
<213> ORGANISM: Homo sapiens

<400> SEQUENCE: 30

Ile Ser Ile Thr Glu Gly Ile Glu Arg
1               5

<210> SEQ ID NO 31
<211> LENGTH: 19
<212> TYPE: PRT
<213> ORGANISM: Homo sapiens

<400> SEQUENCE: 31

Ile Ser Ile Thr Glu Gly Ile Glu Gln Leu Ile Val Asp Ser Ile Thr
1               5                   10                  15

Gly Gln Arg

<210> SEQ ID NO 32
<211> LENGTH: 7
<212> TYPE: PRT
<213> ORGANISM: Homo sapiens

<400> SEQUENCE: 32

Leu Tyr Glu Glu Glu Ile Arg
1               5

<210> SEQ ID NO 33
<211> LENGTH: 8
<212> TYPE: PRT
<213> ORGANISM: Homo sapiens

<400> SEQUENCE: 33

Trp Leu Tyr Glu Glu Glu Ile Arg
1               5
```

```
<210> SEQ ID NO 34
<211> LENGTH: 13
<212> TYPE: PRT
<213> ORGANISM: Homo sapiens

<400> SEQUENCE: 34

Val Leu Gln Ser His Ile Ser Asp Thr Val Val Val Lys
1               5                   10

<210> SEQ ID NO 35
<211> LENGTH: 13
<212> TYPE: PRT
<213> ORGANISM: Homo sapiens

<400> SEQUENCE: 35

Ile Leu Gln Ser His Ile Ser Asp Thr Val Val Val Lys
1               5                   10

<210> SEQ ID NO 36
<211> LENGTH: 11
<212> TYPE: PRT
<213> ORGANISM: Homo sapiens

<400> SEQUENCE: 36

Glu Ala Glu Cys Val Glu Ala Asp Ser Gly Arg
1               5                   10

<210> SEQ ID NO 37
<211> LENGTH: 11
<212> TYPE: PRT
<213> ORGANISM: Homo sapiens

<400> SEQUENCE: 37

Glu Ala Glu Cys Val Glu Ala Asn Ser Gly Arg
1               5                   10

<210> SEQ ID NO 38
<211> LENGTH: 8
<212> TYPE: PRT
<213> ORGANISM: Homo sapiens

<400> SEQUENCE: 38

Asp Val Asp Cys Ala Tyr Leu Arg
1               5

<210> SEQ ID NO 39
<211> LENGTH: 8
<212> TYPE: PRT
<213> ORGANISM: Homo sapiens

<400> SEQUENCE: 39

Asp Val Asp Gly Ala Tyr Leu Arg
1               5

<210> SEQ ID NO 40
<211> LENGTH: 10
<212> TYPE: PRT
<213> ORGANISM: Homo sapiens

<400> SEQUENCE: 40

Ser Ser Ser Phe Ser Cys Gly Ser Ser Arg
1               5                   10
```

```
<210> SEQ ID NO 41
<211> LENGTH: 37
<212> TYPE: PRT
<213> ORGANISM: Homo sapiens

<400> SEQUENCE: 41

Gln Ile Thr Ser Gly Pro Ser Ala Ile Gly Gly Ser Ile Thr Val Val
1               5                   10                  15

Ala Pro Asp Ser Cys Ala Pro Cys Gln Pro Leu Ser Ser Ser Phe Ser
            20                  25                  30

Cys Gly Ser Ser Arg
        35

<210> SEQ ID NO 42
<211> LENGTH: 21
<212> TYPE: PRT
<213> ORGANISM: Homo sapiens

<400> SEQUENCE: 42

Leu Tyr Glu Glu Glu Ile Leu Ile Leu Gln Ser His Ile Ser Asp Thr
1               5                   10                  15

Ser Val Val Val Lys
            20

<210> SEQ ID NO 43
<211> LENGTH: 7
<212> TYPE: PRT
<213> ORGANISM: Homo sapiens

<400> SEQUENCE: 43

Leu Tyr Glu Glu Glu Ile Arg
1               5

<210> SEQ ID NO 44
<211> LENGTH: 14
<212> TYPE: PRT
<213> ORGANISM: Homo sapiens

<400> SEQUENCE: 44

Ile Leu Gln Ser His Ile Ser Asp Thr Ser Val Val Val Lys
1               5                   10

<210> SEQ ID NO 45
<211> LENGTH: 6
<212> TYPE: PRT
<213> ORGANISM: Homo sapiens

<400> SEQUENCE: 45

His Gly Glu Thr Leu Arg
1               5

<210> SEQ ID NO 46
<211> LENGTH: 7
<212> TYPE: PRT
<213> ORGANISM: Homo sapiens

<400> SEQUENCE: 46

His Gly Glu Thr Leu Cys Arg
1               5

<210> SEQ ID NO 47
<211> LENGTH: 16
<212> TYPE: PRT
<213> ORGANISM: Homo sapiens
```

```
<400> SEQUENCE: 47

Gly Leu Thr Gly Gly Phe Gly Ser His Ser Val Cys Gly Gly Phe Arg
1               5                   10                  15

<210> SEQ ID NO 48
<211> LENGTH: 14
<212> TYPE: PRT
<213> ORGANISM: Homo sapiens

<400> SEQUENCE: 48

Gly Leu Thr Gly Gly Phe Gly Ser His Ser Val Cys Gly Arg
1               5                   10

<210> SEQ ID NO 49
<211> LENGTH: 8
<212> TYPE: PRT
<213> ORGANISM: Homo sapiens

<400> SEQUENCE: 49

Leu Leu Glu Gly Glu Glu Gln Arg
1               5

<210> SEQ ID NO 50
<211> LENGTH: 8
<212> TYPE: PRT
<213> ORGANISM: Homo sapiens

<400> SEQUENCE: 50

Leu Leu Glu Gly Lys Glu Gln Arg
1               5

<210> SEQ ID NO 51
<211> LENGTH: 10
<212> TYPE: PRT
<213> ORGANISM: Homo sapiens

<400> SEQUENCE: 51

Asp Asn Ala Glu Leu Glu Asn Leu Ile Arg
1               5                   10

<210> SEQ ID NO 52
<211> LENGTH: 10
<212> TYPE: PRT
<213> ORGANISM: Homo sapiens

<400> SEQUENCE: 52

Asp Asn Ala Glu Leu Lys Asn Leu Ile Arg
1               5                   10

<210> SEQ ID NO 53
<211> LENGTH: 21
<212> TYPE: PRT
<213> ORGANISM: Homo sapiens

<400> SEQUENCE: 53

Leu Asn Val Glu Val Asp Ala Ala Pro Ala Val Asp Leu Asn Gln Val
1               5                   10                  15

Leu Asn Glu Thr Arg
            20

<210> SEQ ID NO 54
<211> LENGTH: 21
<212> TYPE: PRT
<213> ORGANISM: Homo sapiens
```

```
<400> SEQUENCE: 54

Leu Asn Val Glu Val Asp Ala Ala Pro Ala Val Asp Leu Asn Arg Val
1               5                   10                  15

Leu Asn Glu Thr Arg
            20

<210> SEQ ID NO 55
<211> LENGTH: 20
<212> TYPE: PRT
<213> ORGANISM: Homo sapiens

<400> SEQUENCE: 55

Gln Val Val Ser Ser Ser Glu Gln Leu Gln Ser Tyr Gln Ala Glu Ile
1               5                   10                  15

Ile Glu Leu Arg
            20

<210> SEQ ID NO 56
<211> LENGTH: 20
<212> TYPE: PRT
<213> ORGANISM: Homo sapiens

<400> SEQUENCE: 56

Gln Val Val Ser Ser Ser Glu Gln Leu Gln Ser Tyr Gln Val Glu Ile
1               5                   10                  15

Ile Glu Leu Arg
            20

<210> SEQ ID NO 57
<211> LENGTH: 16
<212> TYPE: PRT
<213> ORGANISM: Homo sapiens

<400> SEQUENCE: 57

Thr Val Asn Ala Leu Glu Ile Glu Leu Gln Ala Gln His Asn Leu Arg
1               5                   10                  15

<210> SEQ ID NO 58
<211> LENGTH: 16
<212> TYPE: PRT
<213> ORGANISM: Homo sapiens

<400> SEQUENCE: 58

Thr Leu Asn Ala Leu Glu Ile Glu Leu Gln Ala Gln His Asn Leu Arg
1               5                   10                  15

<210> SEQ ID NO 59
<211> LENGTH: 13
<212> TYPE: PRT
<213> ORGANISM: Homo sapiens

<400> SEQUENCE: 59

Tyr Ser Leu Glu Asn Thr Leu Thr Glu Ser Glu Ala Arg
1               5                   10

<210> SEQ ID NO 60
<211> LENGTH: 13
<212> TYPE: PRT
<213> ORGANISM: Homo sapiens

<400> SEQUENCE: 60

Asp Ser Leu Glu Asn Thr Leu Thr Glu Ser Glu Ala Arg
1               5                   10
```

```
<210> SEQ ID NO 61
<211> LENGTH: 23
<212> TYPE: PRT
<213> ORGANISM: Homo sapiens

<400> SEQUENCE: 61

Tyr Ser Ser Gln Leu Ser Gln Val Gln Ser Leu Ile Thr Asn Val Glu
1               5                   10                  15

Ser Gln Leu Ala Glu Ile Arg
            20

<210> SEQ ID NO 62
<211> LENGTH: 28
<212> TYPE: PRT
<213> ORGANISM: Homo sapiens

<400> SEQUENCE: 62

Tyr Ser Ser Gln Leu Ser Gln Val Gln Ser Leu Ile Thr Asn Val Glu
1               5                   10                  15

Ser Gln Leu Ala Glu Ile His Ser Asp Leu Glu Arg
            20                  25

<210> SEQ ID NO 63
<211> LENGTH: 13
<212> TYPE: PRT
<213> ORGANISM: Homo sapiens

<400> SEQUENCE: 63

Gly Gly Pro Val Gln Val Leu Glu Asp Glu Glu Leu Lys
1               5                   10

<210> SEQ ID NO 64
<211> LENGTH: 10
<212> TYPE: PRT
<213> ORGANISM: Homo sapiens

<400> SEQUENCE: 64

Gly Gly Pro Val Gln Val Leu Glu Asp Lys
1               5                   10

<210> SEQ ID NO 65
<211> LENGTH: 12
<212> TYPE: PRT
<213> ORGANISM: Homo sapiens

<400> SEQUENCE: 65

Glu Leu Asp Val Asp Gly Ile Ile Ala Glu Ile Lys
1               5                   10

<210> SEQ ID NO 66
<211> LENGTH: 12
<212> TYPE: PRT
<213> ORGANISM: Homo sapiens

<400> SEQUENCE: 66

Glu Leu Asp Val Asp Ser Ile Ile Ala Glu Ile Lys
1               5                   10

<210> SEQ ID NO 67
<211> LENGTH: 8
<212> TYPE: PRT
<213> ORGANISM: Homo sapiens
```

<400> SEQUENCE: 67

Asn Glu Ile Leu Glu Met Asn Lys
1               5

<210> SEQ ID NO 68
<211> LENGTH: 8
<212> TYPE: PRT
<213> ORGANISM: Homo sapiens

<400> SEQUENCE: 68

Lys Glu Ile Leu Glu Met Asn Lys
1               5

<210> SEQ ID NO 69
<211> LENGTH: 9
<212> TYPE: PRT
<213> ORGANISM: Homo sapiens

<400> SEQUENCE: 69

Glu Thr Met Gln Phe Leu Asn Asp Arg
1               5

<210> SEQ ID NO 70
<211> LENGTH: 9
<212> TYPE: PRT
<213> ORGANISM: Homo sapiens

<400> SEQUENCE: 70

Glu Ile Met Gln Phe Leu Asn Asp Arg
1               5

<210> SEQ ID NO 71
<211> LENGTH: 8
<212> TYPE: PRT
<213> ORGANISM: Homo sapiens

<400> SEQUENCE: 71

Thr Ile Glu Glu Leu Gln Gln Lys
1               5

<210> SEQ ID NO 72
<211> LENGTH: 8
<212> TYPE: PRT
<213> ORGANISM: Homo sapiens

<400> SEQUENCE: 72

Thr Ile Asp Glu Leu Gln Gln Lys
1               5

<210> SEQ ID NO 73
<211> LENGTH: 8
<212> TYPE: PRT
<213> ORGANISM: Homo sapiens

<400> SEQUENCE: 73

Thr Ile Glu Gln Leu Gln Gln Lys
1               5

<210> SEQ ID NO 74
<211> LENGTH: 9
<212> TYPE: PRT
<213> ORGANISM: Homo sapiens

<400> SEQUENCE: 74

Met Val Val Asn Ile Asp Asn Ala Lys
1               5

<210> SEQ ID NO 75
<211> LENGTH: 9
<212> TYPE: PRT
<213> ORGANISM: Homo sapiens

<400> SEQUENCE: 75

Met Val Val Asn Thr Asp Asn Ala Lys
1               5

<210> SEQ ID NO 76
<211> LENGTH: 16
<212> TYPE: PRT
<213> ORGANISM: Homo sapiens

<400> SEQUENCE: 76

Thr Val Asn Thr Leu Glu Ile Glu Leu Gln Ala Gln His Ser Leu Arg
1               5                   10                  15

<210> SEQ ID NO 77
<211> LENGTH: 17
<212> TYPE: PRT
<213> ORGANISM: Homo sapiens

<400> SEQUENCE: 77

Cys Thr Val Asn Thr Leu Glu Ile Glu Leu Gln Ala Gln His Ser Leu
1               5                   10                  15

Arg

<210> SEQ ID NO 78
<211> LENGTH: 13
<212> TYPE: PRT
<213> ORGANISM: Homo sapiens

<400> SEQUENCE: 78

Asp Ser Leu Glu Asn Thr Leu Thr Glu Ser Glu Ala Arg
1               5                   10

<210> SEQ ID NO 79
<211> LENGTH: 13
<212> TYPE: PRT
<213> ORGANISM: Homo sapiens

<400> SEQUENCE: 79

Asp Ser Leu Glu Asn Met Leu Thr Glu Ser Glu Ala Arg
1               5                   10

<210> SEQ ID NO 80
<211> LENGTH: 23
<212> TYPE: PRT
<213> ORGANISM: Homo sapiens

<400> SEQUENCE: 80

Tyr Ser Ser Gln Leu Ala Gln Met Gln Cys Met Ile Thr Asn Val Glu
1               5                   10                  15

Ala Gln Leu Ala Glu Ile Arg
            20

<210> SEQ ID NO 81
<211> LENGTH: 28
<212> TYPE: PRT
<213> ORGANISM: Homo sapiens

<400> SEQUENCE: 81

Tyr Ser Ser Gln Leu Ala Gln Met Gln Cys Met Ile Thr Asn Val Glu
1               5                   10                  15

Ala Gln Leu Ala Glu Ile Gln Ala Asp Leu Glu Arg
            20                  25

<210> SEQ ID NO 82
<211> LENGTH: 5
<212> TYPE: PRT
<213> ORGANISM: Homo sapiens

<400> SEQUENCE: 82

Ala Asp Leu Glu Arg
1               5

<210> SEQ ID NO 83
<211> LENGTH: 5
<212> TYPE: PRT
<213> ORGANISM: Homo sapiens

<400> SEQUENCE: 83

Ala Glu Leu Glu Arg
1               5

<210> SEQ ID NO 84
<211> LENGTH: 18
<212> TYPE: PRT
<213> ORGANISM: Homo sapiens

<400> SEQUENCE: 84

Ala Glu Leu Glu Arg Gln Asn Gln Glu Tyr Gln Val Leu Leu Asp Asp
1               5                   10                  15

Val Arg

<210> SEQ ID NO 85
<211> LENGTH: 11
<212> TYPE: PRT
<213> ORGANISM: Homo sapiens

<400> SEQUENCE: 85

Ala Arg Leu Glu Gly Glu Ile Asn Thr Tyr Arg
1               5                   10

<210> SEQ ID NO 86
<211> LENGTH: 9
<212> TYPE: PRT
<213> ORGANISM: Homo sapiens

<400> SEQUENCE: 86

Ser Leu Leu Glu Asn Glu Asp Cys Lys
1               5

<210> SEQ ID NO 87
<211> LENGTH: 9
<212> TYPE: PRT
<213> ORGANISM: Homo sapiens

<400> SEQUENCE: 87

Ser Leu Leu Glu Ser Glu Asp Cys Lys
1               5

<210> SEQ ID NO 88

```
<211> LENGTH: 11
<212> TYPE: PRT
<213> ORGANISM: Homo sapiens

<400> SEQUENCE: 88

Ser Ala Tyr Gln Glu Ala Met Asp Ile Ser Lys
1               5                   10

<210> SEQ ID NO 89
<211> LENGTH: 11
<212> TYPE: PRT
<213> ORGANISM: Homo sapiens

<400> SEQUENCE: 89

Ser Ala Tyr Gln Glu Ala Ile Asp Ile Ser Lys
1               5                   10

<210> SEQ ID NO 90
<211> LENGTH: 8
<212> TYPE: PRT
<213> ORGANISM: Homo sapiens

<400> SEQUENCE: 90

Asn Leu Leu Ser Val Ala Tyr Lys
1               5

<210> SEQ ID NO 91
<211> LENGTH: 8
<212> TYPE: PRT
<213> ORGANISM: Homo sapiens

<400> SEQUENCE: 91

Asn Leu Leu Ser Ala Ala Tyr Lys
1               5

<210> SEQ ID NO 92
<211> LENGTH: 11
<212> TYPE: PRT
<213> ORGANISM: Homo sapiens

<400> SEQUENCE: 92

Leu Ala Tyr Gln Glu Ala Met Asp Ile Ser Lys
1               5                   10

<210> SEQ ID NO 93
<211> LENGTH: 11
<212> TYPE: PRT
<213> ORGANISM: Homo sapiens

<400> SEQUENCE: 93

Ser Ala Tyr Gln Glu Ala Ile Asp Ile Ser Lys
1               5                   10

<210> SEQ ID NO 94
<211> LENGTH: 9
<212> TYPE: PRT
<213> ORGANISM: Homo sapiens

<400> SEQUENCE: 94

Glu Met Pro Pro Thr Asn Pro Ile Arg
1               5

<210> SEQ ID NO 95
<211> LENGTH: 9
<212> TYPE: PRT
```

<213> ORGANISM: Homo sapiens

<400> SEQUENCE: 95

Glu Met Pro Pro Ser Asn Pro Ile Arg
1               5

<210> SEQ ID NO 96
<211> LENGTH: 9
<212> TYPE: PRT
<213> ORGANISM: Homo sapiens

<400> SEQUENCE: 96

Glu Met Pro Pro Thr Asn Thr Ile Arg
1               5

<210> SEQ ID NO 97
<211> LENGTH: 11
<212> TYPE: PRT
<213> ORGANISM: Homo sapiens

<400> SEQUENCE: 97

Gly Glu Asp Leu Glu Arg Pro Leu Glu Leu Arg
1               5                   10

<210> SEQ ID NO 98
<211> LENGTH: 11
<212> TYPE: PRT
<213> ORGANISM: Homo sapiens

<400> SEQUENCE: 98

Gly Glu Asp Leu Glu Ser Pro Leu Glu Leu Arg
1               5                   10

<210> SEQ ID NO 99
<211> LENGTH: 13
<212> TYPE: PRT
<213> ORGANISM: Homo sapiens

<400> SEQUENCE: 99

Val Leu Asp Val Asn Asp Asn Phe Pro Thr Leu Glu Lys
1               5                   10

<210> SEQ ID NO 100
<211> LENGTH: 13
<212> TYPE: PRT
<213> ORGANISM: Homo sapiens

<400> SEQUENCE: 100

Val Leu Asp Val Asn Asp Asn Phe Pro Ala Leu Glu Lys
1               5                   10

<210> SEQ ID NO 101
<211> LENGTH: 21
<212> TYPE: PRT
<213> ORGANISM: Homo sapiens

<400> SEQUENCE: 101

Asn Gln Ala Asp Phe His Tyr Ser Val Ala Ser Gln Phe Gln Met His
1               5                   10                  15

Pro Thr Pro Val Arg
            20

<210> SEQ ID NO 102
<211> LENGTH: 20

```
<212> TYPE: PRT
<213> ORGANISM: Homo sapiens

<400> SEQUENCE: 102

Gln Ala Asp Phe His Tyr Ser Val Ala Ser Gln Phe Gln Met Asn Pro
1               5                   10                  15

Thr Pro Val Arg
            20

<210> SEQ ID NO 103
<211> LENGTH: 27
<212> TYPE: PRT
<213> ORGANISM: Homo sapiens

<400> SEQUENCE: 103

Gly Ser Ser Leu Leu Asn Tyr Val Leu Gly Thr Tyr Thr Ala Ile Asp
1               5                   10                  15

Leu Asp Thr Gly Asn Pro Ala Thr Asp Val Arg
            20                  25

<210> SEQ ID NO 104
<211> LENGTH: 26
<212> TYPE: PRT
<213> ORGANISM: Homo sapiens

<400> SEQUENCE: 104

Ser Ser Leu Leu Asn Tyr Val Leu Gly Thr Tyr Thr Ala Ile Asp Leu
1               5                   10                  15

Asp Thr Gly Asn Pro Ala Thr Asp Val Arg
            20                  25

<210> SEQ ID NO 105
<211> LENGTH: 8
<212> TYPE: PRT
<213> ORGANISM: Homo sapiens

<400> SEQUENCE: 105

Ser Ser Thr Met Gly Thr Leu Arg
1               5

<210> SEQ ID NO 106
<211> LENGTH: 8
<212> TYPE: PRT
<213> ORGANISM: Homo sapiens

<400> SEQUENCE: 106

Ser Ser Thr Met Gly Ala Leu Arg
1               5

<210> SEQ ID NO 107
<211> LENGTH: 15
<212> TYPE: PRT
<213> ORGANISM: Homo sapiens

<400> SEQUENCE: 107

Ile Leu Gly Ala Asp Thr Ser Val Asp Leu Glu Glu Thr Gly Arg
1               5                   10                  15

<210> SEQ ID NO 108
<211> LENGTH: 15
<212> TYPE: PRT
<213> ORGANISM: Homo sapiens

<400> SEQUENCE: 108
```

Ile Leu Gly Ala Asp Thr Ser Val Asp Ile Glu Glu Thr Gly Arg
1               5                   10                  15

<210> SEQ ID NO 109
<211> LENGTH: 10
<212> TYPE: PRT
<213> ORGANISM: Homo sapiens

<400> SEQUENCE: 109

Ala Val Asp Ser Leu Val Pro Ile Gly Arg
1               5                   10

<210> SEQ ID NO 110
<211> LENGTH: 10
<212> TYPE: PRT
<213> ORGANISM: Homo sapiens

<400> SEQUENCE: 110

Ala Val Asp Ser Phe Val Pro Ile Gly Arg
1               5                   10

<210> SEQ ID NO 111
<211> LENGTH: 12
<212> TYPE: PRT
<213> ORGANISM: Homo sapiens

<400> SEQUENCE: 111

Thr Ser Ile Ala Ile Asp Thr Ile Ile Asn Gln Lys
1               5                   10

<210> SEQ ID NO 112
<211> LENGTH: 12
<212> TYPE: PRT
<213> ORGANISM: Homo sapiens

<400> SEQUENCE: 112

Thr Ser Ile Ala Val Asp Thr Ile Ile Asn Gln Lys
1               5                   10

<210> SEQ ID NO 113
<211> LENGTH: 22
<212> TYPE: PRT
<213> ORGANISM: Homo sapiens

<400> SEQUENCE: 113

Glu Val Ala Ala Phe Ala Gln Phe Gly Ser Asp Leu Asp Ala Ala Thr
1               5                   10                  15

Gln Gln Leu Leu Ser Arg
            20

<210> SEQ ID NO 114
<211> LENGTH: 7
<212> TYPE: PRT
<213> ORGANISM: Homo sapiens

<400> SEQUENCE: 114

Glu Val Ala Ala Phe Ala Gln
1               5

<210> SEQ ID NO 115
<211> LENGTH: 26
<212> TYPE: PRT
<213> ORGANISM: Homo sapiens

<400> SEQUENCE: 115

Gln Gly Gln Tyr Ser Pro Met Ala Ile Glu Glu Gln Val Ala Val Ile
1               5                   10                  15

Tyr Ala Gly Val Arg Gly Tyr Leu Asp Lys
            20                  25

<210> SEQ ID NO 116
<211> LENGTH: 9
<212> TYPE: PRT
<213> ORGANISM: Homo sapiens

<400> SEQUENCE: 116

Gln Gly Gln Tyr Ser Pro Met Ala Ile
1               5

<210> SEQ ID NO 117
<211> LENGTH: 10
<212> TYPE: PRT
<213> ORGANISM: Homo sapiens

<400> SEQUENCE: 117

Asp Ala Leu Asn Ile Glu Thr Ala Ile Lys
1               5                   10

<210> SEQ ID NO 118
<211> LENGTH: 10
<212> TYPE: PRT
<213> ORGANISM: Homo sapiens

<400> SEQUENCE: 118

Asp Ala Leu Asn Ile Lys Thr Ala Ile Lys
1               5                   10

<210> SEQ ID NO 119
<211> LENGTH: 16
<212> TYPE: PRT
<213> ORGANISM: Homo sapiens

<400> SEQUENCE: 119

Ser Ala Leu Ser Gly His Leu Glu Thr Val Ile Leu Gly Leu Leu Lys
1               5                   10                  15

<210> SEQ ID NO 120
<211> LENGTH: 16
<212> TYPE: PRT
<213> ORGANISM: Homo sapiens

<400> SEQUENCE: 120

Ser Ala Leu Ser Gly His Leu Glu Thr Leu Ile Leu Gly Leu Leu Lys
1               5                   10                  15

<210> SEQ ID NO 121
<211> LENGTH: 17
<212> TYPE: PRT
<213> ORGANISM: Homo sapiens

<400> SEQUENCE: 121

Thr Asp Leu Glu Lys Asp Ile Ile Ser Asp Thr Ser Gly Asp Phe Arg
1               5                   10                  15

Lys

<210> SEQ ID NO 122
<211> LENGTH: 11

```
<212> TYPE: PRT
<213> ORGANISM: Homo sapiens

<400> SEQUENCE: 122

Asp Ile Ile Ser Gly Thr Ser Gly Asp Phe Arg
1               5                   10

<210> SEQ ID NO 123
<211> LENGTH: 14
<212> TYPE: PRT
<213> ORGANISM: Homo sapiens

<400> SEQUENCE: 123

Glu Leu Ser Leu Gly Ile Phe Gly Pro Met Pro Asn Leu Arg
1               5                   10

<210> SEQ ID NO 124
<211> LENGTH: 14
<212> TYPE: PRT
<213> ORGANISM: Homo sapiens

<400> SEQUENCE: 124

Glu Leu Ser Pro Gly Ile Phe Gly Pro Met Pro Asn Leu Arg
1               5                   10

<210> SEQ ID NO 125
<211> LENGTH: 7
<212> TYPE: PRT
<213> ORGANISM: Homo sapiens

<400> SEQUENCE: 125

Asn Thr Asn Ile Ala Gln Lys
1               5

<210> SEQ ID NO 126
<211> LENGTH: 7
<212> TYPE: PRT
<213> ORGANISM: Homo sapiens

<400> SEQUENCE: 126

Asn Thr Asn Phe Ala Gln Lys
1               5

<210> SEQ ID NO 127
<211> LENGTH: 7
<212> TYPE: PRT
<213> ORGANISM: Homo sapiens

<400> SEQUENCE: 127

Val Gln Tyr Asp Leu Gln Lys
1               5

<210> SEQ ID NO 128
<211> LENGTH: 7
<212> TYPE: PRT
<213> ORGANISM: Homo sapiens

<400> SEQUENCE: 128

Val Gln Cys Asp Leu Gln Lys
1               5

<210> SEQ ID NO 129
<211> LENGTH: 11
<212> TYPE: PRT
<213> ORGANISM: Homo sapiens
```

```
<400> SEQUENCE: 129

Pro Cys Val Glu Asn Glu Phe Val Ala Leu Lys
1               5                   10

<210> SEQ ID NO 130
<211> LENGTH: 11
<212> TYPE: PRT
<213> ORGANISM: Homo sapiens

<400> SEQUENCE: 130

Pro Cys Val Gln Asn Glu Phe Val Ala Leu Lys
1               5                   10

<210> SEQ ID NO 131
<211> LENGTH: 21
<212> TYPE: PRT
<213> ORGANISM: Homo sapiens

<400> SEQUENCE: 131

Gly Ala Phe Leu Tyr Glu Pro Cys Gly Val Ser Thr Pro Val Leu Ser
1               5                   10                  15

Thr Gly Val Leu Arg
            20

<210> SEQ ID NO 132
<211> LENGTH: 21
<212> TYPE: PRT
<213> ORGANISM: Homo sapiens

<400> SEQUENCE: 132

Gly Ala Phe Leu Tyr Asp Pro Cys Gly Val Ser Thr Pro Val Leu Ser
1               5                   10                  15

Thr Gly Val Leu Arg
            20

<210> SEQ ID NO 133
<211> LENGTH: 21
<212> TYPE: PRT
<213> ORGANISM: Homo sapiens

<400> SEQUENCE: 133

Gly Ala Phe Leu Tyr Asp Pro Cys Gly Val Ser Met Pro Val Leu Ser
1               5                   10                  15

Thr Gly Val Leu Arg
            20

<210> SEQ ID NO 134
<211> LENGTH: 11
<212> TYPE: PRT
<213> ORGANISM: Homo sapiens

<400> SEQUENCE: 134

Ala Asp Leu Glu Ala Gln Val Glu Ser Leu Lys
1               5                   10

<210> SEQ ID NO 135
<211> LENGTH: 11
<212> TYPE: PRT
<213> ORGANISM: Homo sapiens

<400> SEQUENCE: 135

Ala Asp Leu Glu Ala Gln Val Glu Tyr Leu Lys
```

```
<210> SEQ ID NO 136
<211> LENGTH: 22
<212> TYPE: PRT
<213> ORGANISM: Homo sapiens

<400> SEQUENCE: 136

Leu Pro Cys Asn Pro Cys Ser Thr Pro Ser Cys Thr Thr Cys Val Pro
1               5                   10                  15

Ser Pro Cys Val Thr Arg
            20

<210> SEQ ID NO 137
<211> LENGTH: 22
<212> TYPE: PRT
<213> ORGANISM: Homo sapiens

<400> SEQUENCE: 137

Leu Pro Cys Asn Pro Cys Ser Thr Pro Ser Cys Thr Thr Cys Val Pro
1               5                   10                  15

Ser Pro Cys Val Pro Arg
            20

<210> SEQ ID NO 138
<211> LENGTH: 28
<212> TYPE: PRT
<213> ORGANISM: Homo sapiens

<400> SEQUENCE: 138

Leu Pro Cys Asn Pro Cys Ser Thr Pro Ser Cys Thr Thr Cys Val Pro
1               5                   10                  15

Ser Pro Cys Val Thr Cys Thr Val Cys Val Pro Arg
            20                  25

<210> SEQ ID NO 139
<211> LENGTH: 191
<212> TYPE: PRT
<213> ORGANISM: Homo sapiens

<400> SEQUENCE: 139

Met Gly Thr Trp Ile Leu Phe Ala Cys Leu Leu Gly Ala Ala Pro Ala
1               5                   10                  15

Met Pro Leu Pro Pro His Pro Gly His Pro Gly Tyr Ile Asn Phe Ser
            20                  25                  30

Tyr Glu Val Leu Thr Pro Leu Lys Trp Tyr Gln Ser Ile Arg Pro Pro
        35                  40                  45

Tyr Pro Ser Tyr Gly Tyr Glu Pro Met Gly Gly Trp Leu His His Gln
    50                  55                  60

Ile Ile Pro Val Leu Ser Gln Gln His Pro Thr His Thr Leu Gln
65                  70                  75                  80

Pro His His His Ile Pro Val Val Pro Ala Gln Pro Val Ile Pro
                85                  90                  95

Gln Gln Pro Met Met Pro Val Pro Gly Gln His Ser Met Thr Pro Ile
                100                 105                 110

Gln His His Gln Pro Asn Leu Pro Pro Ala Gln Gln Pro Tyr Gln
            115                 120                 125

Pro Gln Pro Val Gln Pro Gln Pro His Gln Pro Met Gln Pro Gln
        130                 135                 140
```

```
Pro Val His Pro Met Gln Pro Leu Pro Pro Gln Pro Pro Leu Pro Pro
145                 150                 155                 160

Met Pro Pro Met Gln Pro Leu Pro Pro Met Leu Pro Asp Leu Thr Leu
                165                 170                 175

Glu Ala Trp Pro Ser Thr Asp Lys Thr Lys Arg Glu Glu Val Asp
            180                 185                 190

<210> SEQ ID NO 140
<211> LENGTH: 206
<212> TYPE: PRT
<213> ORGANISM: Homo sapiens

<400> SEQUENCE: 140

Met Gly Thr Trp Ile Leu Phe Ala Cys Leu Val Gly Ala Ala Pro Ala
1               5                   10                  15

Met Pro Leu Pro Pro His Pro Gly His Pro Gly Tyr Ile Asn Phe Ser
                20                  25                  30

Tyr Glu Asn Ser His Ser Gln Ala Ile Asn Val Asp Arg Ile Ala Leu
            35                  40                  45

Val Leu Thr Pro Leu Lys Trp Tyr Gln Ser Met Ile Arg Pro Pro Tyr
50                  55                  60

Ser Ser Tyr Gly Tyr Glu Pro Met Gly Gly Trp Leu His His Gln Ile
65                  70                  75                  80

Ile Pro Val Val Ser Gln Gln His Pro Leu Thr His Thr Leu Gln Ser
                85                  90                  95

His His His Ile Pro Val Val Pro Ala Gln Gln Pro Arg Val Arg Gln
                100                 105                 110

Gln Ala Leu Met Pro Val Pro Gly Gln Gln Ser Met Thr Pro Thr Gln
            115                 120                 125

His His Gln Pro Asn Leu Pro Leu Pro Ala Gln Gln Pro Phe Gln Pro
        130                 135                 140

Gln Pro Val Gln Pro Gln Pro His Gln Pro Met Gln Pro Gln Pro Pro
145                 150                 155                 160

Val Gln Pro Met Gln Pro Leu Leu Pro Gln Pro Pro Leu Pro Pro Met
                165                 170                 175

Pro Pro Leu Arg Pro Leu Pro Pro Ile Leu Pro Asp Leu His Leu Glu
            180                 185                 190

Ala Trp Pro Ala Thr Asp Lys Thr Lys Gln Glu Glu Val Asp
        195                 200                 205
```